(12) United States Patent
Connaris et al.

(10) Patent No.: US 11,406,704 B2
(45) Date of Patent: Aug. 9, 2022

(54) ADJUVANTS

(71) Applicant: Pneumagen Limited, Fife (GB)

(72) Inventors: Helen Connaris, St. Andrews (GB);
Garry Taylor, St. Andrews (GB);
Richard E. Randall, St. Andrews (GB)

(73) Assignee: PNEUMAGEN LIMITED, Fife (GB)

( * ) Notice: Subject to any disclaimer, the term of this patent is extended or adjusted under 35 U.S.C. 154(b) by 89 days.

(21) Appl. No.: 16/332,917

(22) PCT Filed: Sep. 20, 2017

(86) PCT No.: PCT/GB2017/052805
§ 371 (c)(1),
(2) Date: Mar. 13, 2019

(87) PCT Pub. No.: WO2018/055370
PCT Pub. Date: Mar. 29, 2018

(65) Prior Publication Data
US 2019/0224311 A1    Jul. 25, 2019

(30) Foreign Application Priority Data
Sep. 20, 2016    (GB) ...................................... 1616007

(51) Int. Cl.
| | |
|---|---|
| A61K 39/00 | (2006.01) |
| A61K 39/39 | (2006.01) |
| C07K 14/28 | (2006.01) |
| C07K 14/315 | (2006.01) |
| C12N 9/28 | (2006.01) |
| A61K 47/64 | (2017.01) |
| A61P 37/04 | (2006.01) |
| A61K 9/00 | (2006.01) |

(52) U.S. Cl.
CPC .............. *A61K 39/39* (2013.01); *A61K 9/006* (2013.01); *A61K 9/0043* (2013.01); *A61K 47/646* (2017.08); *A61P 37/04* (2018.01); *C07K 14/28* (2013.01); *C07K 14/3156* (2013.01); *C12N 9/2417* (2013.01); *C12Y 302/01018* (2013.01); *A61K 2039/541* (2013.01); *A61K 2039/55516* (2013.01); *A61K 2039/6068* (2013.01); *A61K 2039/645* (2013.01); *C07K 2319/735* (2013.01)

(58) Field of Classification Search
CPC ...................................................... A61K 39/39
See application file for complete search history.

(56) References Cited

U.S. PATENT DOCUMENTS

| | | | | |
|---|---|---|---|---|
| 5,004,608 | A * | 4/1991 | Ravdin | C07K 14/44 424/266.1 |
| 2002/0025320 | A1 | 2/2002 | Boyaka et al. | |
| 2004/0072256 | A1 | 4/2004 | Mandelboim et al. | |
| 2005/0084903 | A1 | 4/2005 | Kim et al. | |

FOREIGN PATENT DOCUMENTS

| | | |
|---|---|---|
| EP | 2799086 | 11/2014 |
| WO | 00/10388 | 3/2000 |
| WO | 2002/094869 | 11/2002 |
| WO | 2007/075921 | 7/2007 |
| WO | 2008/053486 | 5/2008 |
| WO | 2010/005737 | 1/2010 |
| WO | 2010/029312 | 3/2010 |
| WO | 2010/052492 | 5/2010 |
| WO | 2010/102112 | 1/2011 |
| WO | 2014/052621 | 4/2014 |
| WO | 2015/110831 | 7/2015 |
| WO | 2018/055365 | 3/2018 |
| WO | 2018/055373 | 3/2018 |

OTHER PUBLICATIONS

Written Opinion and International Search Report corresponding to International Patent Application No. PCT/GB2017/052805, dated Mar. 29, 2018, 11 pages.
International Preliminary Report on Patentability corresponding to International Patent Application No. PCT/GB2017/052805, dated Mar. 26, 2019, 8 pages.
Connaris et al. "Enhancing the Receptor Affinity of the Sialic Acid-binding Domain of Vibrio choleras Sialidase through Multivalency" Journal of Biological Chemistry, 284(11):7339-7351 (2009).
Connaris et al. "Prevention of influenza by targeting host receptors using engineered proteins" Proceedings of the National Academy of Sciences, 111(17):6401-6406 (2014).
International Preliminary Report on Patentability corresponding to International Patent Application No. PCT/GB2017/052800, dated Mar. 26, 2019, 6 pages.
Written Opinion and International Search Report corresponding to International Patent Application No. PCT/GB2017/052800, dated Mar. 29, 2018, 10 pages.
Chen et al. "Preserving Sialic Acid-dependent Pattern Recognition by CD24-Siglec G Interaction for Therapy of Polybacterial Sepsis" Nature Biotechnology, 29(5):428-435 (2011).
Manco et al. "Pneumococcal Neuraminidases A and B Both Have Essential Roles during infection of the Respiratory Tract and Sepsis" Infection and Immunity, 74(7):4014-4020 (2006).
Yang et al. "Structural characterization of the carbobydrate-binding module of NanA sialidase, a pneumococcal virulence factor" BMC Structural Biology, 15(1):15(2015).
Govorkova et al. "Sialic Acid-Binding Protein Sp2CBMTD Protects Mice against Lethal Challenge with Emerging Influenza A (H7N9) Virus" Antimicrobial Agents and Chemothe, American Society for Microbiology, 59(3):1495-1504 (2015).
Written Opinion and Interational Search Report corresponding to International Patent Application No. PCT/GB2017/052808, dated Mar. 29, 2018, 16 pages.

(Continued)

*Primary Examiner* — Albert M Navarro
(74) *Attorney, Agent, or Firm* — Myers Bigel, P.A.

(57) ABSTRACT

The present disclosure provides novel adjuvants which may be used in combination with one or more antigens to augment, modulate or enhance a host immune response to the one or more antigens. The adjuvants are based on sialic acid binding molecules and may be combined with any type of antigen. The adjuvants may be formulated for mucosal and/or intranasal administration.

12 Claims, 17 Drawing Sheets
Specification includes a Sequence Listing.

(56) References Cited

OTHER PUBLICATIONS

International Preliminary Report on Patentability corresponding to International Patent Application No. PCT/GB2017/052808, dated Mar. 26, 2019, 9 pages.
Simmons et al. "Regression of Established Methylcholanthrene Tumors by Intratumor Injections of Vibrio Cholerae Neuraminidase" Journal of Surgical Onco, 4(4):298-305 (1972) Abstract.
Simmons et al. "Immunospecific Regression of Methylcholanthrene Fibrosarcoma With the Use of Neuraminidase. II. Intratumor Injections of Neuraminidase" Sur, 71(4):556-564 (1972).
Grata-Borkowska et al. "Effects of neuraminidase on apoptosis of blood lymphocytes in rats with implanted Morris tumor" Journal of physiology and pharmacology: an official journal of the Polish Physiological Society, p. 253, URL: http://www.jpp.krakow.pl/journal/archive/11_07_s5/pdf/253_11_07_s5_article.pdf (2007).
Gasiorowski et al. "The impact of neuraminidase on apoptosis in cultures of blood lymphocytes isolated from rats bearing morris hepatoma" Cellular & molecular biology letters, pp. 389-399, URL: http://www.cmbl.org.pl/pdf/Vol9_p389.pdf (2004).
Baradaran et al. "Newcastle Disease Virus Hemagglutinin Neuraminidase as a potential Cancer Targeting Agent", Journal of Cancer, 7,(4):462-466 (2016).
Alias "Multivalent sialic acid binding proteins as novel therapeutics for influenza and parainfluenza infection" PhD Thesis at University of St Andrews, 252 pages (2013).
Knop "Stimulatory effect of Vibrio cholera neuraminidase on the antibody response to various antigens" Immunology, 34:181-187 (1978).
Research Councils UK, Gateway to Research "Exploiting a sialic acid binding domain" University of St Andrews, 4 pages, accessed Jun. 1, 2017 from http://gtr.rcuk.ac.uk/projects?ref=BB%FE001912%2F1.
Rios et al. "Experimental Cancer Immunotherapy: modification of tumor cells to increase immunogenicity" Annals New York Academy of Sciences, 276:45-60 (1976).
Simmons et al. "Immunospecific Regression of Methylcholanthrene Fibrosarcoma With the Use of Neuraminidase: III. Synergistic Effect of BCG and Neuraminidase Treated Tumor Cells" Ann. Surg., 176(2):188-194 (1972).

\* cited by examiner

A.
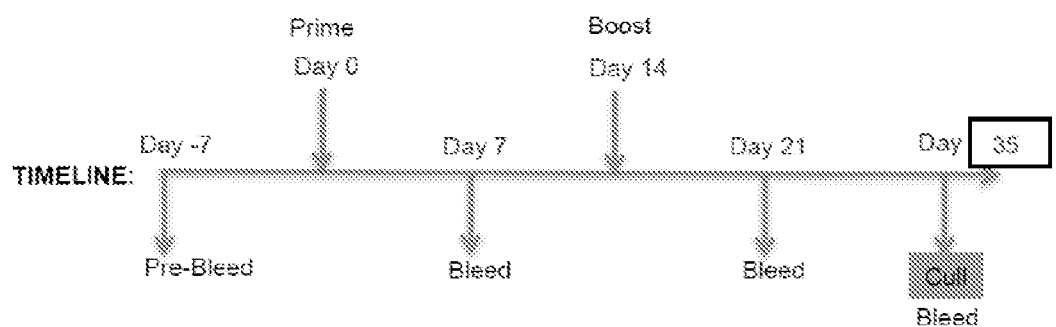
B.
Dosing groups:
| Groups | Antigens (µg) | | | | |
|---|---|---|---|---|---|
| | GFP | GFP-Sp2CBMTD | GFP-Vc2CBMTD | Sp2CBMTD | Vc2CBMTD |
| 1 | | | | | |
| 2 | 0.7 | | | | |
| 3 | | 2 | | | |
| 4 | | | 2 | | |
| 5 | 0.7 | | | 1.3 | |
| 6 | 0.7 | | | | 1.3 |
| 7 | | | | 1.3 | |
| 8 | | | | | 1.3 |
Figure 5 (A & B)

Figure 7A:
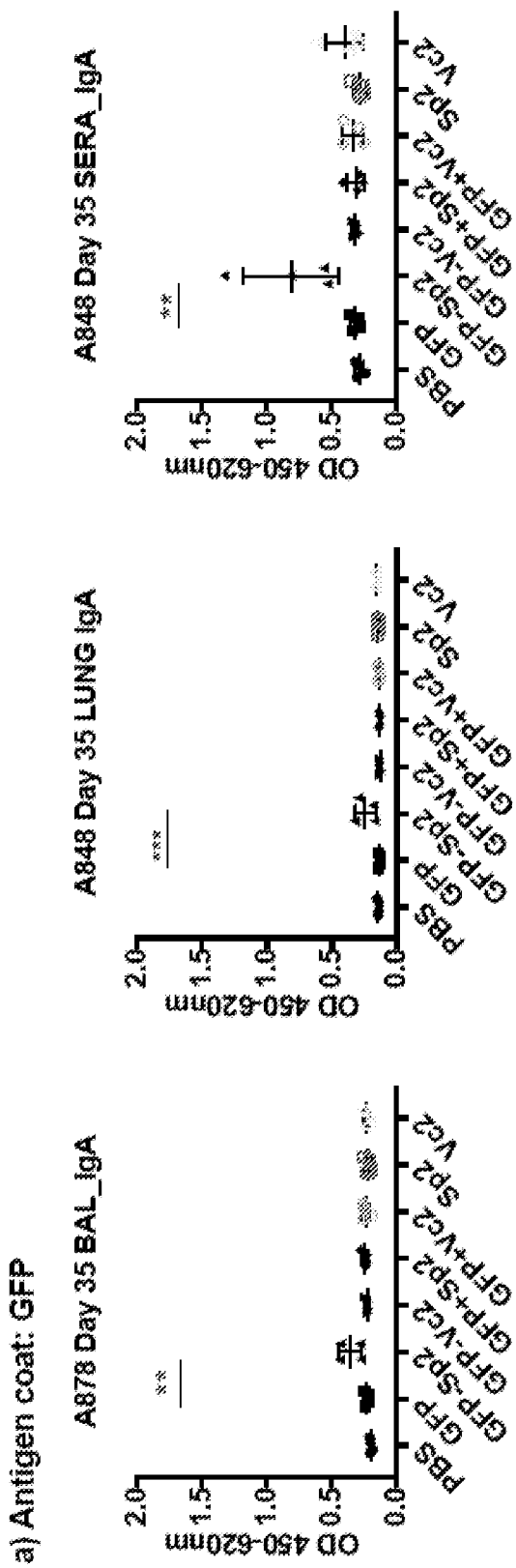
Figure 7A:
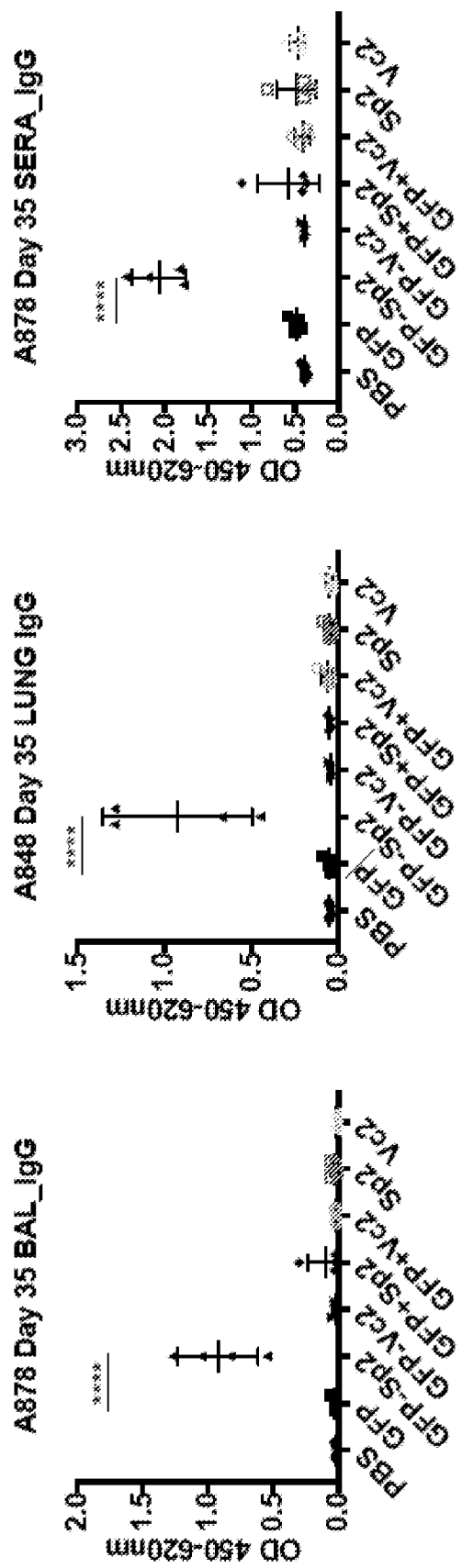
Figure 7B:
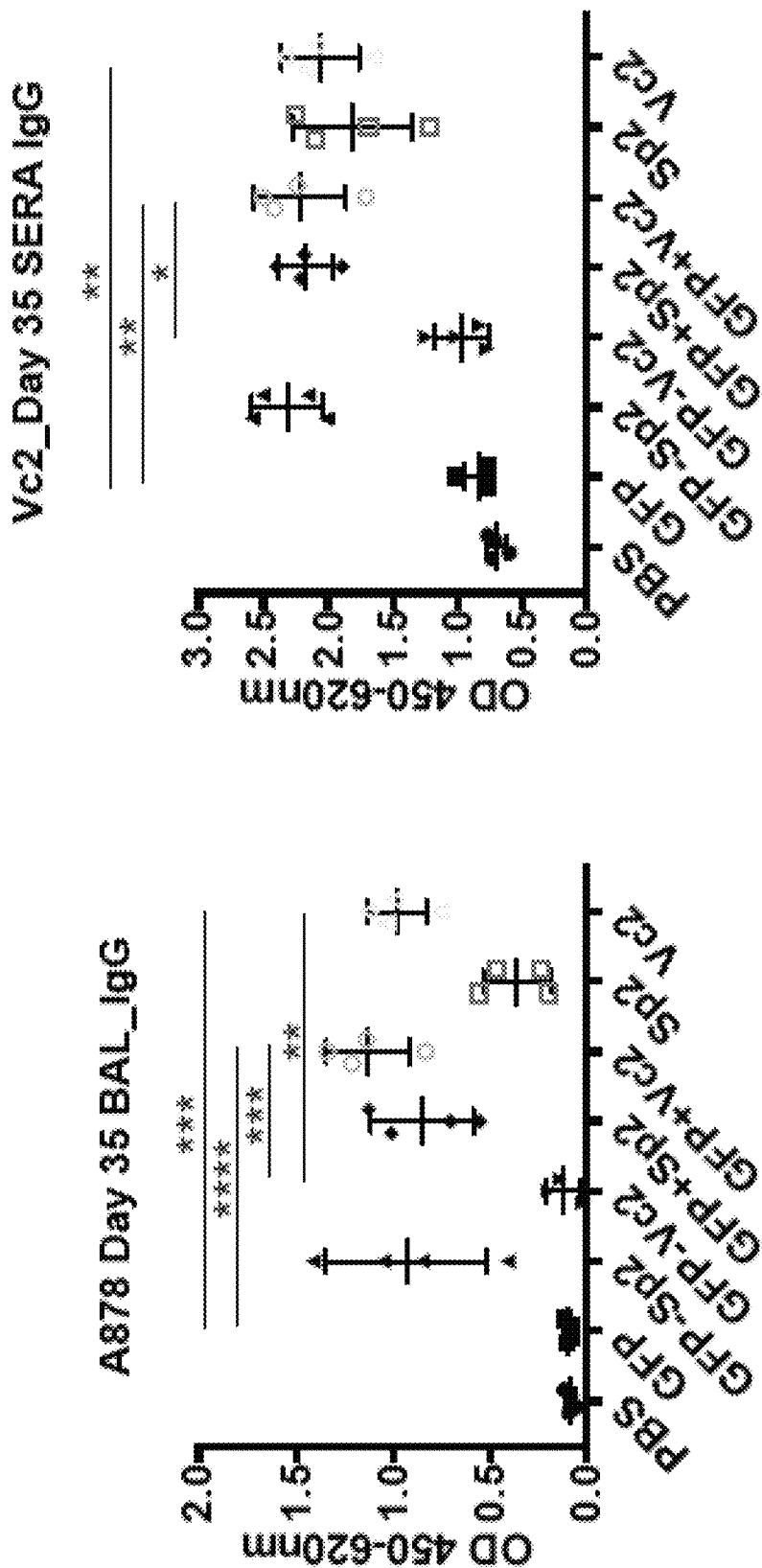
Figure 7C:
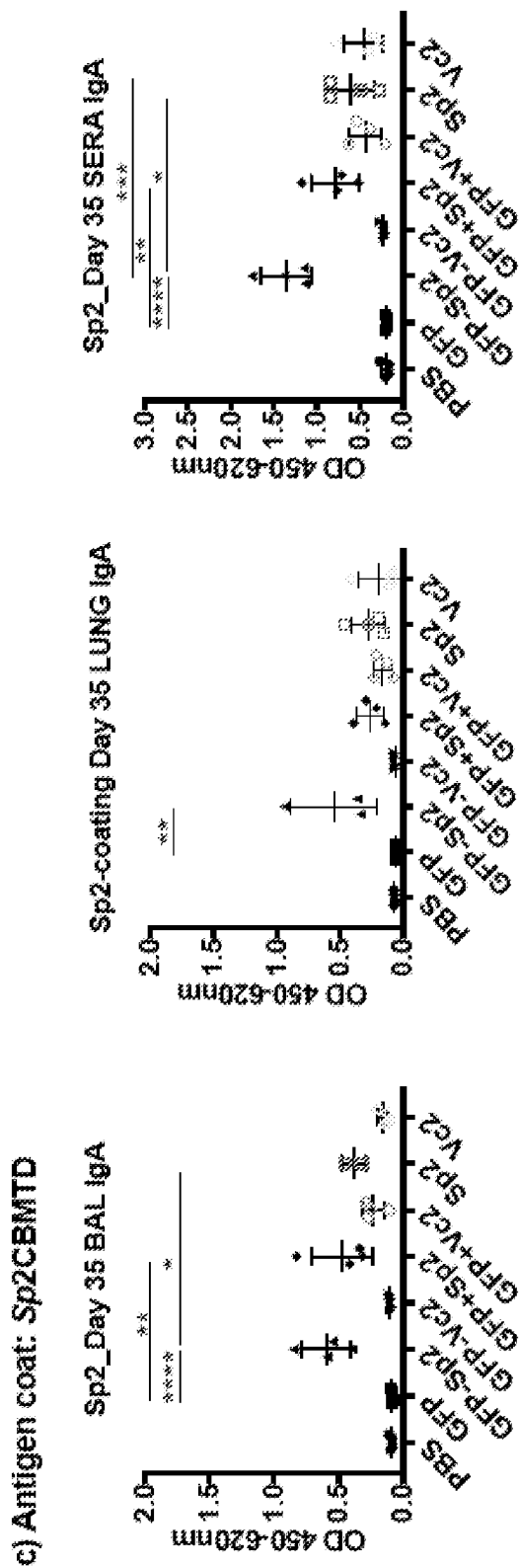
Figure 7D:
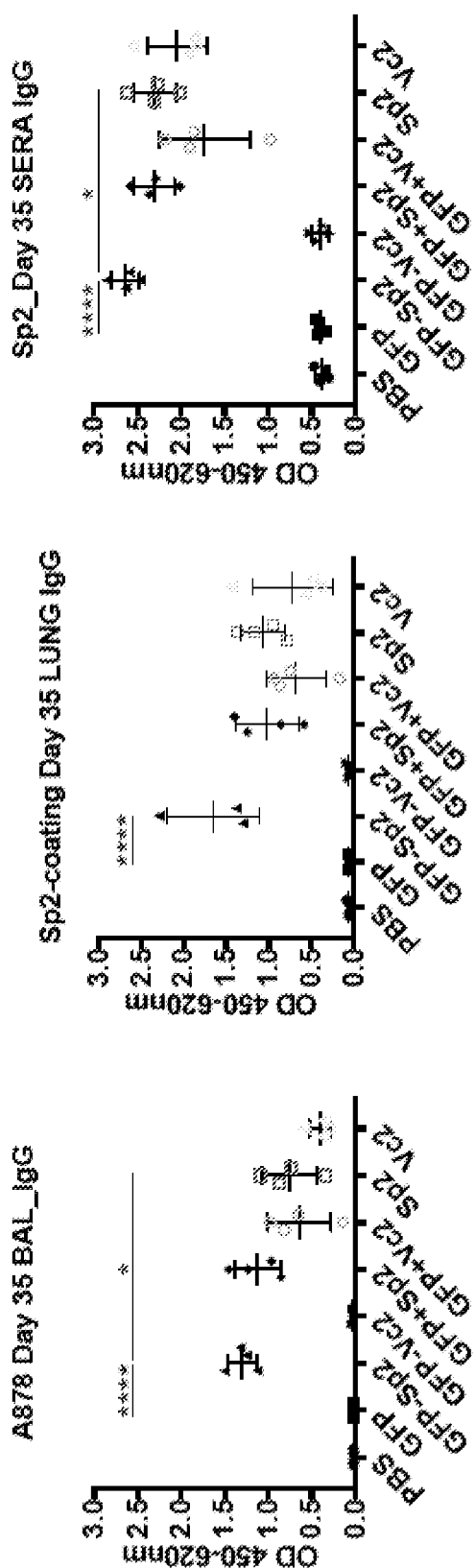

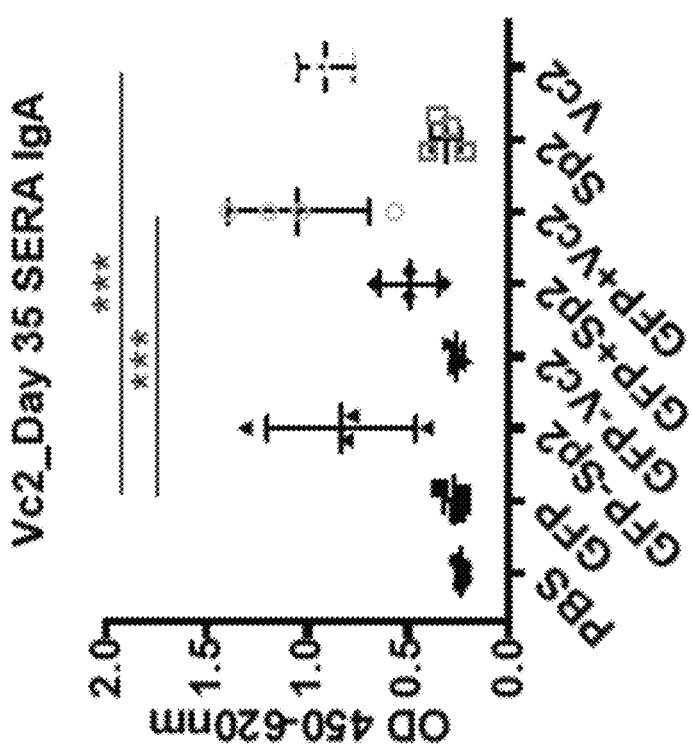
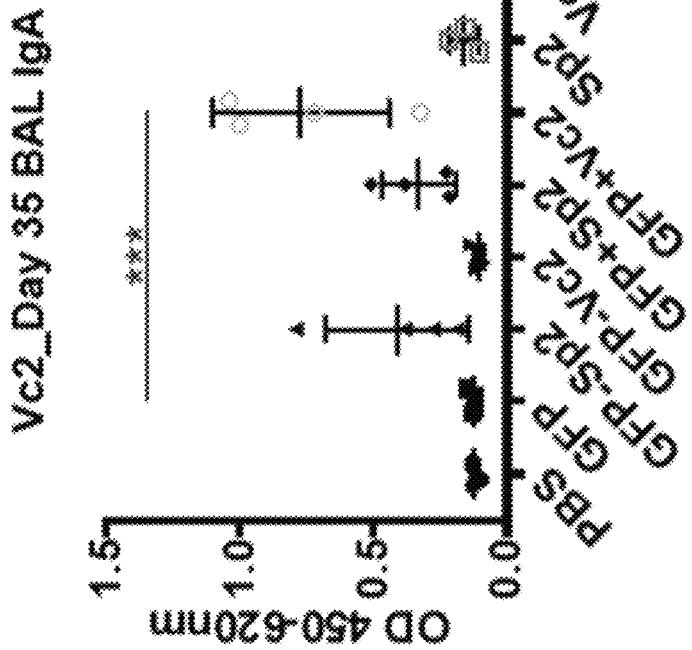
Figure 7B

ADJUVANTS

STATEMENT OF PRIORITY

This application is a 35 U.S.C. § 371 national phase application of International Application Serial No. PCT/GB2017/052805, filed Sep. 20, 2017, which claims the benefit, of United Kingdom Patent Application No. 1616007.9, filed Sep. 20, 2016 the entire contents of each of which are incorporated by reference herein.

FIELD OF THE INVENTION

The present invention provides adjuvants for use with antigens and vaccines. The adjuvants described herein comprise sialic acid binding molecules and are useful as mucosal adjuvants where they can be used to ensure not only a subject mucosally-administered an antigen raises a strong and suitable mucosal immune response, but that that subject also raises a systemic immune response to the same antigen.

BACKGROUND OF THE INVENTION

The majority of vaccines in use today are delivered by injection and the resulting systemic immunity represents an important aspect of the host's armoury against pathogens; however, this route is less effective in inducing an immune response at mucosal surfaces. A mucosal immune response is desirable as vaccines often target pathogens that enter their host through the mucosal surfaces. For example, a number of pathogens that cause or contribute to respiratory diseases, including for example influenza, attach to and ultimately enter host cells via receptors present on the surface of cells of the mucosal membranes. Mucosal immune responses (which in humans comprise an IgA response) therefore represent a first line defence against these pathogens and thus vaccines, which induce protective mucosal immune responses, are desirable.

The advantages of a mucosal vaccine over vaccines administered by injection include, for example, ease of administration, a non-invasive nature and the ability to induce immunity across a large tissue surface area.

While systemic and mucosal immunity are important in their own right, a truly effective and protective immune response should comprise both mucosal and systemic immune responses. In humans, the aim might be to induce IgA, IgM and IgG immune responses via a single vaccine and a single route of administration.

However, while vaccines delivered by injection often don't raise sufficient (or indeed any) mucosal immune response, vaccines that are delivered mucosally may not induce a sufficient systemic immune response.

Adjuvants can be used to augment, improve, expand and/or modify the immune response raised by a vaccine. For example by combining a vaccine composition (which may comprise one or more antigens) with an adjuvant, it is possible to induce a better (more protective) immune response and perhaps even an immune response which extends through multiple tissues, systems and sites—for example an immune response which comprises both a systemic (blood borne) and a mucosal immune response. Any improvement in the immune response induced by a vaccine combined with an adjuvant would be in comparison to the level or extent of immunity induced by the vaccine alone (i.e. without adjuvant).

There is a need for adjuvants, which can be combined with vaccines to ensure that the vaccines deliver the required immune response. There is a further need for adjuvants, which can be administered with mucosal vaccines to ensure that the vaccine induces not only a local mucosal immune response, but also a systemic immune response.

SUMMARY OF THE INVENTION

Disclosed herein are novel adjuvants, which may be used in combination with one or more antigens to augment, modulate or enhance a host immune response to the one or more antigens. It should be noted that while the adjuvants disclosed herein can be combined with any type of antigen, the adjuvants, which are the subject of this disclosure are especially for use with antigens that are to be administered mucosally. Accordingly, the adjuvants of this invention may be referred to hereinafter as "mucosal adjuvants".

It should be understood that throughout this specification, the terms "comprise", "comprising" and/or "comprises" is/are used to denote aspects and embodiments of this invention that "comprise" a particular feature or features. It should be understood that this/these terms may also encompass aspects and/or embodiments which "consist essentially of" or "consist of" the relevant feature or features.

The adjuvants disclosed herein comprise compounds, which exhibit an ability to (or are capable of) binding sialic acid and/or moieties (for example cell receptors and other molecules) comprising the same. Compounds of this type shall be referred to hereinafter as sialic acid binding molecules.

Thus, disclosed herein are adjuvants, for example mucosal adjuvants, which comprise, consist essentially of, or consist of, sialic acid binding molecules.

Sialic acid binding molecules with utility as adjuvants may otherwise be used to neutralise or prevent infection by pathogens that are able to bind sialic acid and/or which exploit sialic acid containing receptors on the surface of host cells. For example, respiratory pathogens such as viruses belonging to the Orthomyxoviridae or Paramyxoviridae families and certain *Streptococcus* bacteria exploit the presence of sialic acid in cell surface receptors as a means to bind and gain entry to specific cell types in a variety of mammalian tissues. Without wishing to be bound by theory, a molecule which binds to sialic acid may interfere with and/or inhibit, prevent and/or block the interaction between a pathogen and a sialic acid moiety and/or a cell surface receptor containing sialic acid; the sialic acid binding molecule may therefore prevent the pathogen from binding and/or adhering. Thus compounds, for example proteins and peptides, which bind to sialic acid moieties and/or to molecules (for example cell surface receptors) comprising the same, may therefore be used in the treatment and/or prevention of diseases caused or contributed to by pathogens which exploit cell surface sialic acid containing receptors.

The inventors have now discovered that in addition to binding to sialic acid and interfering with or blocking, preventing and/or inhibiting the interaction between a pathogen and, for example, a sialic acid containing molecule or cell surface receptor, sialic acid binding molecules possess adjuvant properties and when administered together with one or more antigens, has an adjuvant effect.

Compounds with adjuvant properties (i.e. adjuvants) are often added to vaccines. Many different types of vaccine are currently in use and many of these are formulated/combined or administered (concurrently or separately) with adjuvants to improve, augment or modify the nature of the immune response raised against the antigen component of the vaccine. In some cases, an adjuvant is exploited as a means to improve an immune response in a human or animal host. For example an adjuvant may be used to improve the immune response raised by low (sub-optimal) doses of antigen. In this regard, an adjuvant/adjuvant composition of this invention may be combined with sub-optimal doses of a vaccine or antigen—the vaccine or antigen serving to increase the immune response raised by the sub-optimal antigen dose. When administered together or with an adjuvant or adjuvant composition of this invention, the immune response raised by a sub-optimal vaccine/antigen dose, may be comparable to an immune response raised by administration of an optimal dose of vaccine/antigen alone (i.e. without adjuvant). Adjuvants are particularly useful when the antigen component of a vaccine is poorly or insufficiently immunogenic in its own right. Antigens which are sufficiently immunogenic may not require to be administered in combination with an adjuvant as administration of the antigen alone raises or induces, for example, a protective and/or neutralising immune response (a "neutralising immune response" comprising, for example, antibodies which bind to certain parts of a pathogen and to prevent them from binding their usual receptors and a "protective immune response" comprising antibodies which are able to neutralise a pathogen and resolve an infection but possibly also lead to the opsonisation and/or clearance/destruction of a pathogen).

However, certain types of antigen may be poorly or insufficiently immunogenic. For example, certain proteinaceous antigens, in particular those that contain concealed epitopes or domains, which mimic certain host (or self) peptides and/or protein domains, may exhibit an insufficient level of immunogenicity when administered. Additionally, antigens that comprise significant amounts of carbohydrate material (or which consist (essentially) of carbohydrate material) might be less immunogenic than antigens, which are more proteinaceous in nature. Where the antigen (carbohydrate in nature or otherwise) is not sufficiently immunogenic in its own right, an adjuvant might be used to improve, augment or modify the immune response raised or induced upon administration of the antigen to a host.

In other instances, an adjuvant might be used to ensure that an immune response is raised in a specific tissue or at a specific site. One of skill will appreciate that whereas administration of an antigen might easily induce a local immune response—the locality of the immune response being restricted to the site of administration, that immune response may not be widespread in the host. For example, an antigen administered to a mucosal tissue may only raise a mucosal immune response. The induced mucosal immune response may offer adequate protection to the host throughout the mucosal surfaces/tissues, but the induced immune response may not also embrace a systemic immune response. In such cases an adjuvant may be used to ensure that any immune response raised is not merely a local immune response and confined to the site or tissue to which the antigen is administered. By way of example, an adjuvant may be used with an antigen that is to be administered mucosally for the purpose of inducing not only a local mucosal immune response, but also a systemic response.

In humans, certain antigens administered mucosally might only induce an IgA response (IgA being the predominant antibody isotype of the mucous membranes). When administered mucosally and in combination with an adjuvant, that same antigen might also induce a systemic IgM and/or IgG based response.

By combining antigens with the sialic acid binding molecule-based adjuvants of this invention, and administering the combination mucosally (for example intranasally), it is possible to ensure the induction not only of a mucosal immune response to the antigen component of the vaccine but also immune responses to the antigen in or at other tissues, systems and sites. For example the combined mucosal administration of an antigen and a sialic acid binding molecule-based adjuvant may result not only in a mucosal immune response to the antigen but also a systemic immune response to the same antigen.

In view of the above, the present disclosure provides an adjuvant comprising a molecule capable of binding sialic acid (a "sialic acid binding molecule").

The adjuvants of this disclosure may comprise one or more different types of sialic acid binding molecule.

In a second aspect, the disclosure provides the use of sialic acid binding molecules as adjuvants.

In a third aspect, the disclosure provides an adjuvant composition comprising a sialic acid binding molecule, any necessary additional adjuvant components including, for example, other adjuvants approved for mucosal administration. Suitable "other" adjuvants will be known to one of skill in this field and may include, for example; microbial toxin/toxoid based adjuvants, TLR ligands, non-TLR immunostimulants, novel small molecules, oil-based adjuvants and organic adjuvants. An adjuvant composition of this disclosure may further comprise a pharmaceutically or physiologically acceptable excipient, diluent, solvent or carrier.

As stated, the sialic acid binding molecule-based adjuvants described herein may be added to vaccines and/or vaccine compositions. As such, the present invention provides vaccines (for human and/or animal use), comprising or formulated with, a sialic acid binding molecule-based adjuvant of this invention. The vaccine may be further formulated for mucosal administration. For example, the vaccine may be formulated for administration to a mucosal surface. For example, the vaccine may be formulated for oral, intranasal, vaginal and/or rectal delivery. Thus the invention provides sialic acid binding molecule-based adjuvant supplemented mucosal vaccines. Without wishing to be bound by theory, the sialic acid binding protein-based adjuvants disclosed herein may be added to a vaccine or vaccine composition as a means to improve, augment or modify the effect of the vaccine/vaccine composition when it is administered. For example, a vaccine to which an adjuvant of this disclosure is added may induce a better (for example more protective and/or more widespread) immune response to the antigen component thereof as compared to the immune response raised by the same vaccine administered without the adjuvant.

Mucosal vaccines (that is, vaccines that are administered mucosally and which raise a mucosal immune response) represent an advantage over other, perhaps parenterally administered vaccines. In addition to the fact that mucosal vaccines are sometimes easier to administer than vaccines administered by other routes, a strong, effective and/or protective mucosal immune response is often desirable as it represents a first line defence against a number of pathogens, which enter the host via the host mucosal surfaces. Parenterally administered vaccines often do not induce a sufficient level of (or indeed any level of) mucosal immunity. Further, mucosal vaccines often only induce local, mucosal immune responses and while a mucosal response is often effective against those fungal, bacterial and/or viral pathogens, which colonise and invade through or via a mucosal surface (including, for example those collectively referred to as respiratory pathogens), it is often preferable that vaccines raise both local and systemic immune responses (for example mucosal and systemic immune responses).

The provision of an adjuvant, which can be combined with a mucosal vaccine, allows the user to benefit from the convenience of a mucosal route of administration so as to generate a strong mucosal immune response but with the confidence that the vaccine (although only administered mucosally) will also raise a systemic immune response.

For example, a mucosal vaccine comprising an antigen or antigens from one or more pathogens/respiratory pathogen(s) may be supplemented with a sialic acid-based adjuvant of this invention. The respiratory pathogen(s) from which the antigen(s) is/are derived may cause or contribute to a disease or condition which affects some part of the respiratory system including, for example the respiratory mucosal surfaces and/or the lungs. In this way, the vaccine will induce not only a mucosal (IgA (in humans) based) immune response, but also a systemic (IgM and/or IgG (in humans) based) immune response. One of skill will appreciate that while a mucosal response may be sufficiently protective, a systemic immune response offers an additional level of protection, which can help resolve infections that manage to get beyond the mucosal surfaces and into deeper tissues and/or systems.

Examples of pathogens (for example respiratory pathogens) from which antigen(s) might be derived (for use in vaccines) and against which mucosal and/or systemic immune responses might be effective, include (but are not limited to) viruses belonging to the group known as the 'retroviruses' (including, for example HIV), the Picornavirales (including Rhinovirus species), Flaviviridae, Coronaviridae, Adenoviridae (including Adenovirus species), Orthomyxoviridae (including influenza viruses A, B and C) or Paramyxoviridae families, certain bacteria including, for example those species belonging to the *Streptococcus, Staphylococcus, Corynebacterium, Klebsiella, Pseudomonas, Haemophilus, Legionella, Mycobacterium*, and *Neisseria* genera and certain fungal pathogens including, for example, those of the *Aspergillus* genus. As stated, the adjuvants of this disclosure may be used in combination with any antigens (whether or not derived from the above list of pathogens) and thus this list of respiratory pathogens should not be construed as in anyway limiting. In effect, the adjuvants described herein may be used in combination with any antigen that can be administered mucosally.

The term "antigens" may also embrace cancer or tumour antigens. Thus the adjuvants of this invention may be used in combination with one or more cancer or tumour antigens.

As described in more detail later, the adjuvants described herein may be administered together or concurrently with, an antigen(s) or a vaccine. Concurrent administration may involve administering the antigen(s)/vaccine and adjuvant together and at the same time (co-administration) or together in the form of a conjugate or fusion. For example, the adjuvant may be fused or conjugated to the antigen (or alternatively, the antigen(s) may be fused or conjugated to the adjuvant). Where the sialic acid binding molecule based adjuvant is fused to the antigen, the fusion may be at the N- and/or C-terminal end of the antigen. Alternatively (or additionally) the adjuvant may be placed somewhere within the antigen. Where there are multiple antigens, one or more of the antigens may be provided as a fusion and the fusions (in terms of where the fusion between the antigen and adjuvant occurs (at the N- and/or C-terminal end of the antigen or internally within the antigen)) may be the same or different. The adjuvants disclosed herein comprise sialic acid binding molecules and the term "sialic acid" embraces all forms of N- or O-substituted neuraminic acid and includes all synthetic, naturally occurring and/or modified forms thereof. Sialic acids may be found as components of cell surface molecules, glycoproteins and glycolipids. Most often, sialic acids are present at the end (terminal regions) of sugar chains connected to cell membranes and/or proteins. For example, some cells of the human upper respiratory tract comprise α-2,6-linked sialic acid receptors and other cells of the upper and lower respiratory tracts comprise α-2,3-linked sialic acid receptors. The sialic acid family encompasses a number (approximately 50) of derivatives that may result from acetylation, glycolylation, lactonisation and methylation at C4, C5, C7, C8 and C9. All such derivatives are to be embraced by the term "sialic acid".

Furthermore, sialic acids are found linked α(2,3) or α(2,6) to Gal and GalNAc or α(2,8) or α(2,9) to another sialic acid. Accordingly, it is important to understand that while the term "sialic acid" is used throughout this specification, it encompasses all derivatives, analogues or variants (either naturally occurring or synthetically generated) thereof as well as monomers, dimers, trimers, oligomers, polymers or concatamers comprising the same.

Thus an adjuvant of this disclosure comprises a sialic acid binding molecule, which exhibits an affinity for sialic acid—including all forms of sialic acid described above and sialic acid present on the surface of mammalian cells.

It should be understood that molecules, which exhibit an affinity for sialic acid, bind to or otherwise couple to or associate with sialic acid moieties. Thus the term "sialic acid binding molecule" may further encompass any fragment of a whole sialic acid binding molecule, which retains an ability to bind to or otherwise couple or associate with sialic acid.

The adjuvants disclosed herein may comprise a single molecule capable of binding sialic acid (a monomeric or monovalent molecule, for example) or, alternatively, two or more sialic acid binding molecules (which may all be the same or different—a polymeric or multivalent molecule, for example).

The adjuvants may comprise one or more sialic acid binding molecules known as "carbohydrate binding modules" (CBMs). CBMs suitable for use as adjuvants may exhibit an affinity for sialic acid. Exemplary carbohydrate binding modules for use in this invention may comprise the sialic acid binding domain of *Vibrio cholerae* NanH sialidase (VcCBM) and/or the equivalent (or homologous) domain from *Streptococcus pneumoniae* NanA sialidase (SpCBM). Of course, similar or homologous sialic acid binding modules present in other organisms are to be encompassed within the scope of the term "CBM". This may include, for example CBMs with a function and/or sequence which is homologous to any of the specific CBMs described herein.

Thus, this disclosure provides adjuvants, which comprise, consist essentially of or consist of one or more CBM(s).

The disclosure further provides an adjuvant or vaccine/vaccine composition comprising:
 (i) one or more sialic acid binding molecules; and/or
 (ii) one or more CBM(s); and/or
 (iii) the sialic acid binding domain of *Vibrio cholerae* NanH sialidase (VcCBM); and/or
 (iv) the sialic acid binding domain of *Streptococcus pneumoniae* NanA sialidase (SpCBM).

The disclosure further provides vaccines and vaccine compositions comprising one or more antigens and one or more adjuvants selected from the group of adjuvants which comprise, consist essentially of or consist of:
 (i) one or more sialic acid binding molecules; and/or
 (ii) one or more CBM(s); and/or (iii) the sialic acid binding domain of *Vibrio cholerae* NanH sialidase (VcCBM); and/or
(iv) the sialic acid binding domain of *Streptococcus pneumoniae* NanA sialidase (SpCBM).

By way of example vaccines and vaccine compositions against, for example, forms of 'flu', diphtheria, Whooping cough, measles, mumps, rubella, polio, tuberculosis, meningitis, tetanus, yellow fever, rabies (to name a few) may be combined, used or administered with any of the adjuvants described herein. The adjuvants of this disclosure may also be combined or used with any mucosally administered vaccine, including, for example, those mucosally administered influenza vaccines.

An exemplary *Vibrio cholerae* NanH sialidase amino acid sequence is deposited under accession number A5F7A4 and is reproduced below as SEQ ID NO: 1 (781 amino acids).

```
MRFKNVKKTA LMLAMFGMAT SSNAALFDYN
ATGDTEFDSP AKQGWMQDNT NNGSGVLTNA
DGMPAWLVQG IGGRAQWTYS LSTNQHAQAS
SFGWRMTTEM KVLSGGMITN YYANGTQRVL
PIISLDSSGN LVVEFEGQTG RTVLATGTAA
TEYHKFELVF LPGSNPSASF YFDGKLIRDN
IQPTASKQNM IVWGNGSSNT DGVAAYRDIK
FEIQGDVIFR GPDRIPSIVA SSVTPGVVTA
FAEKRVGGGD PGALSNTNDI ITRTSRDGGI
TWDTELNLTE QINVSDEFDF SDPRPIYDPS
SNTVLVSYAR WPTDAAQNGD RIKPWMPNGI
FYSVYDVASG NWQAPIDVTD QVKERSFQIA
GWGGSELYRR NTSLNSQQDW QSNAKIRIVD
GAANQIQVAD GSRKYVVTLS IDESGGLVAN
LNGVSAPIIL QSEHAKVHSF HDYELQYSAL
NHTTTLFVDG QQITTWAGEV SQENNIQFGN
ADAQIDGRLH VQKIVLTQQG HNLVEFDAFY
LAQQTPEVEK DLEKLGWTKI KTGNTMSLYG
NASVNPGPGH GITLTRQQNI SGSQNGRLIY
PAIVLDRFFL NVMSIYSDDG GSNWQTGSTL
PIPFRWKSSS ILETLEPSEA DMVELQNGDL
LLTARLDFNQ IVNGVNYSPR QQFLSKDGGI
TWSLLEANNA NVFSNISTGT VDASITRFEQ
SDGSHFLLFT NPQGNPAGTN GRQNLGLWFS
FDEGVTWKGP IQLVNGASAY SDIYQLDSEN
AIVIVETDNS NMRILRMPIT LLKQKLTLSQ
N
```

The CBM region of SEQ ID NO: 1 is from amino acid residue 25 to 216—this sequence may be SEQ ID NO: 2.

An exemplary *Streptococcus pneumoniae* NanA sialidase amino acid sequence has been deposited under accession number P62575 and is reproduced below as SEQ ID NO: 3 (1035 amino acids).

```
MSYFRNRDID IERNSMNRSV QERKCRYSIR
KLSVGAVSMI VGAVVFGTSP VLAQEGASEQ
PLANETQLSG ESSTLTDTEK SQPSSETELS
GNKQEQERKD KQEEKIPRDY YARDLENVET
VIEKEDVETN ASNGQRVDLS SELDKLKKLE
NATVHMEFKP DAKAPAFYNL FSVSSATKKD
EYFTMAVYNN TATLEGRGSD GKQFYNNYND
APLKVKPGQW NSVTFTVEKP TAELPKGRVR
LYVNGVLSRT SLRSGNFIKD MPDVTHVQIG
ATKRANNTVW GSNLQIRNLT VYNRALTPEE
VQKRSQLFKR SDLEKKLPEG AALTEKTDIF
ESGRNGKPNK DGIKSYRIPA LLKTDKGTLI
AGADERRLHS SDWGDIGMVI RRSEDNGKTW
GDRVTITNLR DNPKASDPSI GSPVNIDMVL
VQDPETKRIF SIYDMFPEGK GIFGMSSQKE
EAYKKIDGKT YQILYREGEK GAYTIRENGT
VYTPDGKATD YRVVVDPVKP AYSDKGDLYK
GNQLLGNIYF TTNKTSPFRI AKDSYLWMSY
SDDDGKTWSA PQDITPMVKA DWMKFLGVGP
GTGIVLRNGP HKGRILIPVY TTNNVSHLNG
SQSSRIIYSD DHGKTWHAGE AVNDNRQVDG
QKIHSSTMNN RRAQNTESTV VQLNNGDVKL
FMRGLTGDLQ VATSKDGGVT WEKDIKRYPQ
VKDVYVQMSA IHTMHEGKEY IILSNAGGPK
RENGMVHLAR VEENGELTWL KHNPIQKGEF
AYNSLQELGN GEYGILYEHT EKGQNAYTLS
FRKFNWDFLS KDLISPTEAK VKRTREMGKG
VIGLEFDSEV LVNKAPTLQL ANGKTARFMT
QYDTKTLLFT VDSEDMGQKV TGLAEGAIES
MHNLPVSVAG TKLSNGMNGS EAAVHEVPEY
TGPLGTSGEE PAPTVEKPEY TGPLGTSGEE
PAPTVEKPEY TGPLGTAGEE AAPTVEKPEF
TGGVNGTEPA VHEIAEYKGS DSLVTLTTKE
DYTYKAPLAQ QALPETGNKE SDLLASLGLT
AFFLGLFTLG KKREQ
```

The CBM region of SEQ ID NO: 3 is from amino acid residue 121 to 305—this sequence may be SEQ ID NO: 4.

As such, the adjuvants disclosed herein may comprise a protein or peptide having the sequence of SEQ ID NO: 1 or 2 or a sialic acid binding fragment thereof. For example, a useful adjuvant may comprise a proteinaceous moiety encoded by the sialic acid binding domain of the nanH gene (encoding sialidase) of *V. cholerae* or an equivalent or homologous gene present in another organism (for example the equivalent/homologous nanA sialidase gene of *S. pneu-* moniae). For example, a sialic acid binding molecule of this invention may comprise from about residue 1, 5, 10, 15, 25 or 30 (i.e. from 1-30 or from any amino acid residue there between) to about residue 150, 175, 200, 210, 216, 220-781 (to any residue from 150 to 781 including any residue therebetween) of the *V. cholerae* sialidase molecule of SEQ ID NOS: 1 and 2. For example an adjuvant for use may comprise a peptide having a sequence corresponding to residue 25 to about residue 216 of SEQ ID NO: 1 above.

A further suitable adjuvant may comprise a protein or peptide having the sequence of SEQ ID NO: 3 or 4 or a sialic acid binding fragment thereof. For example, a useful adjuvant may comprise a proteinaceous moiety encoded by the sialic acid binding domain of the *Streptococcus pneumoniae* nanA gene (encoding sialidase). For example a sialic acid binding molecule of this invention may comprise from about residue 80, 90, 100, 110, 120, 121 to 130 (i.e. from any of about residues 80 to 130 including any residue therebetween) to about residue 250, 275, 300, 305, 310, 320-1035 (i.e. to any residue from about 250-1035 including to about any residue therebetween) of the *S. pneumoniae* sialidase molecule of SEQ ID NOS: 3 and 4. For example and adjuvant for use may comprise a peptide having a sequence corresponding to residue 121 to about residue 305 of SEQ ID NO: 3 above.

An adjuvant for use may comprise one or more CBMs. For example, suitable adjuvants may comprise single CBMs—for example, a single VcCBM or a single SpCBM. Alternatively, the adjuvants may comprise a plurality or multiple (i.e. two or more) CBMs. Sialic acid binding molecules, which comprise a plurality of CBMs may be termed "multivalent sialic acid binding molecules" or "multivalent CBMs". A multivalent CBM may, for example, comprise two or more VcCBMs or two or more SpCBMs. A multivalient CBM may comprise a mixture of different CBMs, for example one or more VcCBMs with one or more SpCBMs. Thus an adjuvant disclosed herein may comprise a multivalent CBM.

For example, multivalent CBM molecules, (for example a Vc4CBM molecule) may be prepared as constructs comprising multiple CBMs linked by amino acid/peptide linkers. Each CBM (for example VcCBM) may be linked to another by, for example, peptides comprising 5, 10 or 15 amino acids. By way of example any one or more of the following peptides may be used to link two or more CBMs to produce a multivalent CBM:

```
(i) 5 amino acid linkers:
ALNGS
LQALG
GGNSG (ii) 10 amino acid linkers:
ALNGSGGGSG
LQALGGGGSL (iii) 15 amino acid linkers:
ALNGSGGGSGGGGSG
```

An adjuvant for use may further comprise an oligomerisation domain. Suitable oligomerisation domains may exhibit an ability to self-associate to form multimer structures, for example trimers. An oligomerisation domain for use as an adjuvant of this disclosure may comprise any molecule with the above mentioned oligomerisation properties or any functional fragment thereof. For example one or more (for example two) sialic acid binding molecules (for example CBMs) may be bound, coupled or fused to an oligomerisation domain—the resulting sialic acid binding molecule/oligomerisation domain "fusion" may then be used (with one or more other such "fusions" as an adjuvant).

Suitable oligomerisation domains may be derived from, for example, *Pseudomonas aeruginosa* pseudaminidase. An exemplary *Pseudomonas aeruginosa* pseudaminidase sequence amino acid sequence has been deposited under accession number PAO579 and is reproduced below as SEQ ID NO: 5 (438 amino acids).

```
MNTYFDIPHR LVGKALYESY YDHFGQMDIL
SDGSLYLIYR RATEHVGGSD GRVVFSKLEG
GIWSAPTIVA QAGGQDFRDV AGGTMPSGRI
VAASTVYETG EVKVYVSDDS GVTWVHKFTL
ARGGADYNFA HGKSFQVGAR YVIPLYAATG
VNYELKWLES SDGGETWGEG STIYSGNTPY
NETSYLPVGD GVILAVARVG SGAGGALRQF
ISLDDGGTWT DQGNVTAQNG DSTDILVAPS
LSYIYSEGGT PHVVLLYTNR TTHFCYYRTI
LLAKAVAGSS GWTERVPVYS APAASGYTSQ
VVLGGRRILG NLFRETSSTT SGAYQFEVYL
GGVPDFESDW FSVSSNSLYT LSHGLQRSPR
RVVVEFARSS SPSTWNIVMP SYFNDGGHKG
SGAQVEVGSL NIRLGTGAAV WGTGYFGGID
NSATTRFATG YYRVRAWI
```

The oligomerisation domain of SEQ ID NO: 5 is from amino acid residue 333 to 438—this sequence may be SEQ ID NO: 6.

Thus an oligomerisation domain for use in an adjuvant of this disclosure may comprise from about residue 250, 275, 300, 310, 320, 333, 340 to 350 (i.e. from about residue 250 to about residue 350 including from about any residue therebetween) to about residue 400, 410, 420, 430 or 438 (i.e. to about any residue from about residue 400 residue 438 including to about any residue therebetween) of the *P. aeruginosa* pseudaminidase trimerisation domain (PaTD) provided by SEQ ID NO: 5. For example, a useful adjuvant may exploit oligomerisation domains comprising residues 333 to 438 of SEQ ID NO: 6.

Thus this invention provides adjuvants comprising, for example, one or more VcCBM or SpCBM for use in or with vaccines and vaccine compositions.

An adjuvant may comprise one or more of the CBM based molecules presented in FIG. 1.

For example, a suitable adjuvant may comprise (consist essentially of, or consist of) two or more VcCBMs optionally fused, bound or conjugated to an oligomerisation domain (such as a PaTD or oligomerisation fragment thereof). The adjuvant may comprise, consist or consist essentially of two fused (or bound) VcCBMs, which are in turn, fused to an oligomerisation domain (see, for example, molecule Vc2CBMTD shown in FIG. 1).

Other adjuvants for use may comprise two or more SpCBMs optionally fused, bound or conjugated to an oligomerisation domain (such as a PaTD or an oligomerisation fragment thereof). The adjuvant may comprise, consist or consist essentially of two fused (or bound) SpCBMs, which are in turn, fused to an oligomerisation domain (see, for example, molecule Sp2CBMTD shown in FIG. 1).

Figure 1:
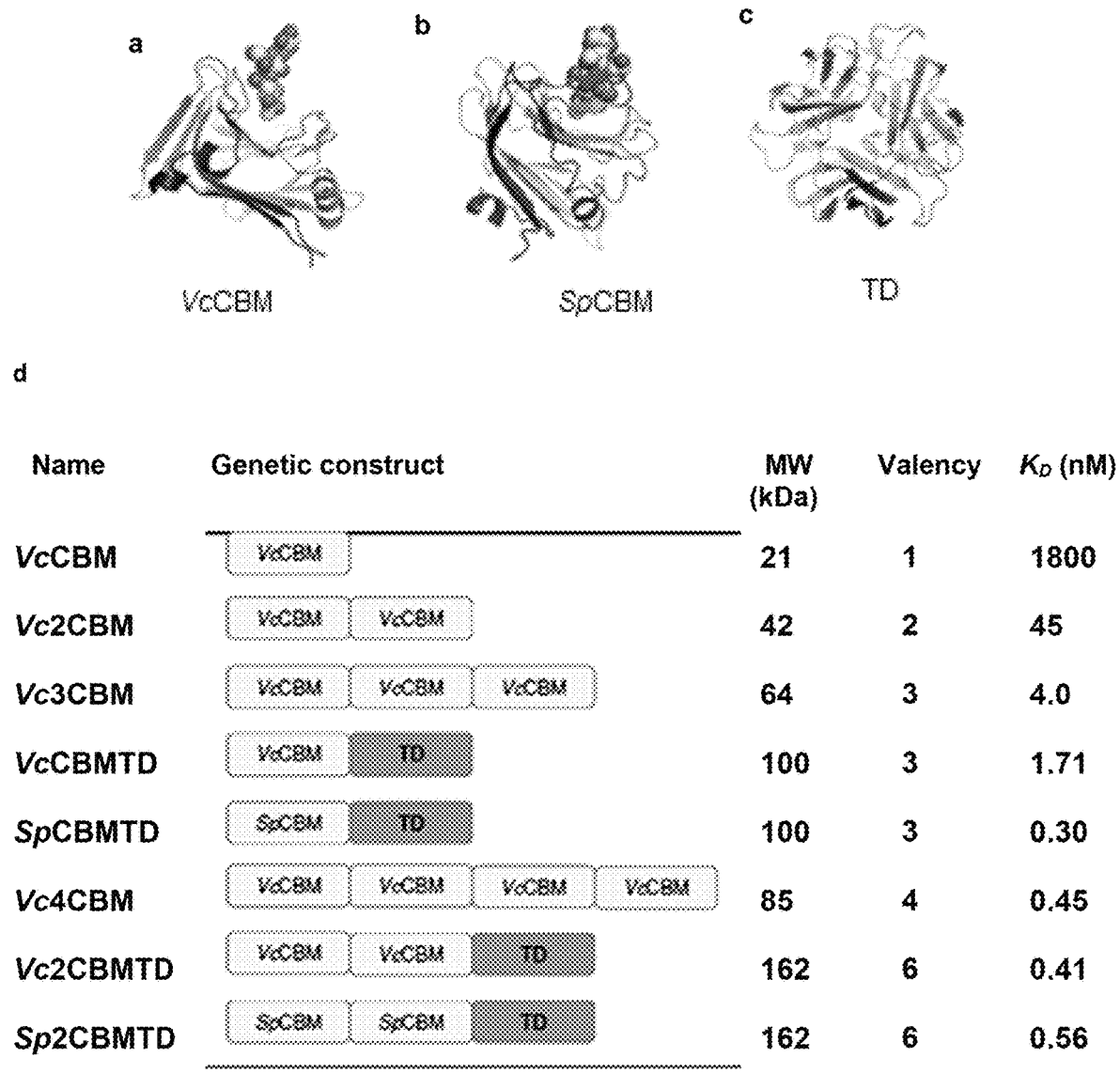

It should be understood that the various multivalent CBMs (including Vc2CBMTD and Sp2CBMTD as shown in FIG. 1) may find application in methods of modulating immune responses in subjects, the methods comprising the administration of an immunomodulatory amount of the multivalent CBM.

Also provided, are sialic acid-binding molecule (for example CBM)-based adjuvants for use in enhancing immune responses in human or animal subjects. As stated, the adjuvants described herein may be administered together or concurrently with, an antigen(s) or a vaccine. The adjuvants may be formulated together with a vaccine for administration to a human or animal subject. However, the adjuvants for use may be formulated as separate compositions (together with suitable pharmaceutical carriers, diluents and/or excipients) to be administered to human or animal subjects before or after administration of a vaccine.

Also provided are methods of raising immune responses and/or methods of enhancing, modulating or augmenting immune responses in human or animal subjects, said methods comprising the step of administering a vaccine and a sialic acid binding molecule (for example CBM)-based adjuvant disclosed herein, to a human or animal subject in need thereof. The adjuvant may be administered mucosally and may be formulated with the vaccine such that it is administered to a human or animal host therewith or as a separate composition such that it can be administered separately from the vaccine or concurrently therewith.

It is stated above that the adjuvants may be provided with suitable excipients, diluents and/or carriers. Suitable excipients may include, for example oil and one of skill will appreciate that the term "oil" may include alkanes, alkenes, alkynes, and their corresponding acids and alcohols, the ethers and esters thereof, and mixtures thereof. The individual compounds of the oil are light hydrocarbon compounds, i.e., such components have 6 to 30 carbon atoms. The oil can be synthetically prepared or purified from petroleum products. The "oil" may have a straight or branched chain structure. It may be fully saturated or have one or more double or triple bonds. Some non-metabolizable oils for use in the present invention include mineral oil, paraffin oil, and cycloparaffins, for example.

The term oil is also intended to include "light mineral oil," i.e., oil which is similarly obtained by distillation of petrolatum, but which has a slightly lower specific gravity than white mineral oil. Other "oil" for use as excipients may include metabolizable (non-toxic) oils. Oils of this type may include, for example vegetable oils, fish oils, animal oils or synthetically prepared oils which can be metabolized by the body of the subject (human or animal) to which the adjuvant will be administered and which are non-toxic. Sources for vegetable oils include nuts, seeds and grains.

One of skill will appreciate that any of the oil excipients described herein may be provided as oil-in-water, water-in-oil or water-in-oil-in-water emulsion forms.

An oil-in-water emulsion may comprise an AMPHIGEN® formulation. This formulation comprises an aqueous component, lecithin, mineral oil, and surfactants. Patents describing the components of the formulation include U.S. Pat. Nos. 5,084,269 and 6,572,861, the contents of which are incorporated herein by reference. Typically, the oil component of the present invention is present in an amount from 1% to 50% by volume; or in an amount of 10% to 45%; or in an amount from 20% to 40%.

Other components of the adjuvant compositions described herein can include pharmaceutically acceptable excipients, such as carriers, solvents, and diluents, isotonic agents, buffering agents, stabilizers, preservatives, vaso-constrictive agents, antibacterial agents, antifungal agents, and the like. Typical carriers, solvents, and diluents include water, saline, dextrose, ethanol, glycerol, oil, and the like. Representative isotonic agents include sodium chloride, dextrose, mannitol, sorbitol, lactose, and the like. Useful stabilizers include gelatin, albumin, and the like.

Surfactants are often used to assist in the stabilization of an emulsion selected to act as the carrier for the adjuvant and any antigen. Surfactants suitable for use with the adjuvants described herein may include natural biologically compatible surfactants and non-natural synthetic surfactants. Biologically compatible surfactants include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

Non-natural, synthetic surfactants suitable for use with the adjuvants described herein include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL M-53®), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctyl phenyl ethers (TRITON® X). Generally speaking, the surfactant, or the combination of surfactants, if two or more surfactants are used, is present in the emulsion in an amount of 0.01% to 10% by volume, preferably, 0.1% to 6.0%, more preferably 0.2% to 5.0%.

As used herein, the term "a pharmaceutically-acceptable carrier" includes any and all solvents, dispersion media, coatings, stabilizing agents, diluents, preservatives, antibacterial and antifungal agents, isotonic agents, adsorption delaying agents, and the like that might be used with an adjuvant. The carrier(s) should be "acceptable" in the sense of being compatible with the other components of the compositions and not deleterious to the subject. Typically, the carriers will be sterile and pyrogen-free, and selected based on the mode of administration to be used. It is well known by those skilled in the art that certain formulations of pharmaceutically acceptable carrier comprise those carriers approved in the applicable regulations promulgated by the United States (US) Department of Agriculture or US Food and Drug Administration, or equivalent government agency in a non-US country. Therefore, the pharmaceutically accepted carrier for commercial production of an adjuvant composition according to this invention may be a carrier that is already approved or will be approved by the appropriate government agency in the US or foreign country.

Useful adjuvant compositions may optionally include compatible pharmaceutically acceptable (i.e., sterile or non-toxic) liquid, semisolid, or solid diluents that serve as pharmaceutical vehicles, excipients, or media. Diluents can include water, saline, dextrose, ethanol, glycerol, and the like. Isotonic agents can include sodium chloride, dextrose, mannitol, sorbitol, and lactose, among others. Stabilizers include albumin, among others.

Suitable adjuvant compositions can also contain antibiotics or other preservatives, including, for example, gentamicin, merthiolate, or chlorocresol. The various classes of antibiotics or preservatives from which to select are well known to the skilled artisan.

Adjuvant compositions provided herein may also comprise one or more additional adjuvant components. For example, an adjuvant composition may, in addition to the sialic acid binding molecules (for example CBMs) described herein, comprise one or more adjuvants selected from the group consisting of alum (comprising aluminium hydroxide/phosphate); oil-based adjuvants and organic adjuvants (for example squalene).

The adjuvant and/or adjuvant compositions described herein may be provided in lyophilised form or as lyophilised compositions. One of skill will appreciate that lyophilised adjuvant/adjuvant compositions of this invention may be reconstituted (for example prior to use) using any of the pharmaceutically acceptable carriers/diluents and/or excipients described herein.

Advantageously, the adjuvants and adjuvant compositions described herein may further comprise one or more preservative agents—including, for example, a cryopreservative agent.

The disclosure further provides a kit comprising an adjuvant of this invention and, optionally a vaccine and instructions for the preparation of the adjuvant, vaccine and/or a formulation for administration comprising the adjuvant and vaccine. The kit may comprise diluent, buffer, carrier, solvent and/or excipients for preparation of the adjuvant and/or vaccine. The kit may further comprise tools and equipment required for the preparation of the vaccine, adjuvant and/or vaccine/adjuvant composition and for the delivery or administration of the same to a subject. For example, the kit may include a syringe and various vials. The adjuvant and/or vaccine components of the kit may be provided in the form of products prepared by a spray drying method or encapsulated. Additionally, or alternatively, the adjuvant/vaccine components of the kit may be provided in lyophilised form for reconstitution prior to use.

The adjuvants (which comprise any of the sialic acid binding molecules (for example any of the CBM type molecules)) described herein, may be used in any suitable amount. Further, the adjuvants may be formulated for oral, mucosal or parenteral administration—the precise formulation may depend on the formulation of the antigen(s) with which the adjuvant is to be administered. For example a vaccine (comprising one or more antigens) that is to be administered mucosally may require the use of an adjuvant which is also formulated for mucosal administration. This may not always be the case and it is possible that the adjuvant could be administered via a route different to that of the antigen. The amount of adjuvant used may vary and in some cases may comprise an amount from about 0.1 μg to about 100 μg. For example about 0.2 μg, 0.3 μg, 0.4 μg, 0.5 μg, 1 μg, 1.1 μg, 1.2 μg, 1.3 μg, 1.4 μg, 1.5 μg, 2 μg, 5 μg, 10 μg, 20 μg, 30 μg, 40 μg, 50 μg, 60 μg, 70 μg, 80 μg, 90 μg or 95 μg of the sialic acid binding molecule (CBM) based adjuvant may be used. The amount of adjuvant may be formulated within a suitable volume of a pharmaceutically acceptable excipient, diluent or buffer. The excipient, diluent or buffer may be sterile and/or pyrogen (endotoxin) free. Suitable excipient, diluent or buffer volumes may include, for example, volumes of about 1 μl to about 5 ml. For example, the required amount of sialic acid binding molecule (CBM) based adjuvant may be combined (or formulated) with about 5 μl, 10 μl, 15 μl, 20 μl, 25 μl, 30 μl, 35 μl, 40 μl, 45 μl, 50 μl, 55 μl, 60 μl, 65 μl, 70 μl, 75 μl, 80 μl, 85 μl, 90 μl, 95 μl, 100 μl, 200 μl, 300 μl, 400 μl, 500 μl, 600 μl, 700 μl, 800 μl, 900 μl, 1 ml, 2 ml, 3 ml or 4 ml. For example, when an adjuvant of this disclosure is to be administered intranasally about 1 μg, 1.3 μg, 2 μg or 10 μg (for example) may be used in about 20 μl, 30 μl, 40 μl or 50 μl of a suitable excipient, diluent or buffer. Where the adjuvant is a fusion, the total amount of protein used in any given dose may be about 0.1 μg to about 100 μg. For example about 0.2 μg, 0.3 μg, 0.4 μg, 0.5 μg, 1 μg, 1.1 μg, 1.2 μg, 1.3 μg, 1.4 μg, 1.5 μg, 2 μg, 5 μg, 10 μg, 20 μg, 30 μg, 40 μg, 50 μg, 60 μg, 70 μg, 80 μg, 90 μg or 95 μg.

In use, the adjuvant may be administered multiple times over a number of days or weeks. For example after an initial (or first) administration, the adjuvant may be administered again at about (+/−1 or 2 days) 3, 4, 5, 6, 7, 17, 21, 28 or 35 days later. On any given day, a specific dose of adjuvant may be administered 1, 2, 3 or more times. Each time, the adjuvant may be administered (by whatever route is considered best) with or without the antigen to which it is hoped an immune response will be raised.

This disclosure further provides an adjuvant which comprising any one or more of the sialic acid binding molecules described herein. The disclosure also provides any one or more of the sialic acid binding molecules described herein for use as an adjuvant.

The disclosure also relates to a composition comprising an antigen and any of the sialic acid binding molecules described herein for use in raising an immune response in a human or animal subject. The raised immune response may be a mucosal immune response. The composition (for use in raising an immune response) may be a vaccine, for example a mucosal vaccine.

Also described herein is a vaccine comprising an antigen and any one or more of the sialic acid binding molecules described herein, wherein the molecule capable of binding sialic acid is used (or included) in the vaccine as an adjuvant.

DETAILED DESCRIPTION OF THE INVENTION

The disclosure will now be described in detail by reference to the following figures, which show:

FIG. 1: Building blocks of the multivalent CBM forms and their affinities for sialic acid. a, VcCBM, residues 25-216 of the *V. cholerae* sialidase (PDB:1w0p) with α-2,3-sialyllactose drawn as spheres. b, SpCBM, residues 121-305 of *S. pneumoniae* NanA sialidase with α-2,3-sialyllactose (PDB:4c1w). c, TD, the trimerisation domain, residues 333-438, of the *P. aeruginosa* pseudaminidase (PDB:2w38) in rainbow colours; the other two monomers in single colours. d, Multivalent forms: their molecular weights, valencies and binding affinities for α2,3-sialyllactose as determined by surface plasmon resonance (SPR) at 25° C. (KD values for VcCBM, Vc2CBM and Vc3CBM had been reported previously 78). Tandem repeat CBMs, and oligomeric CBMs fused to TD are linked by a 5-amino linker.

Figure 2:
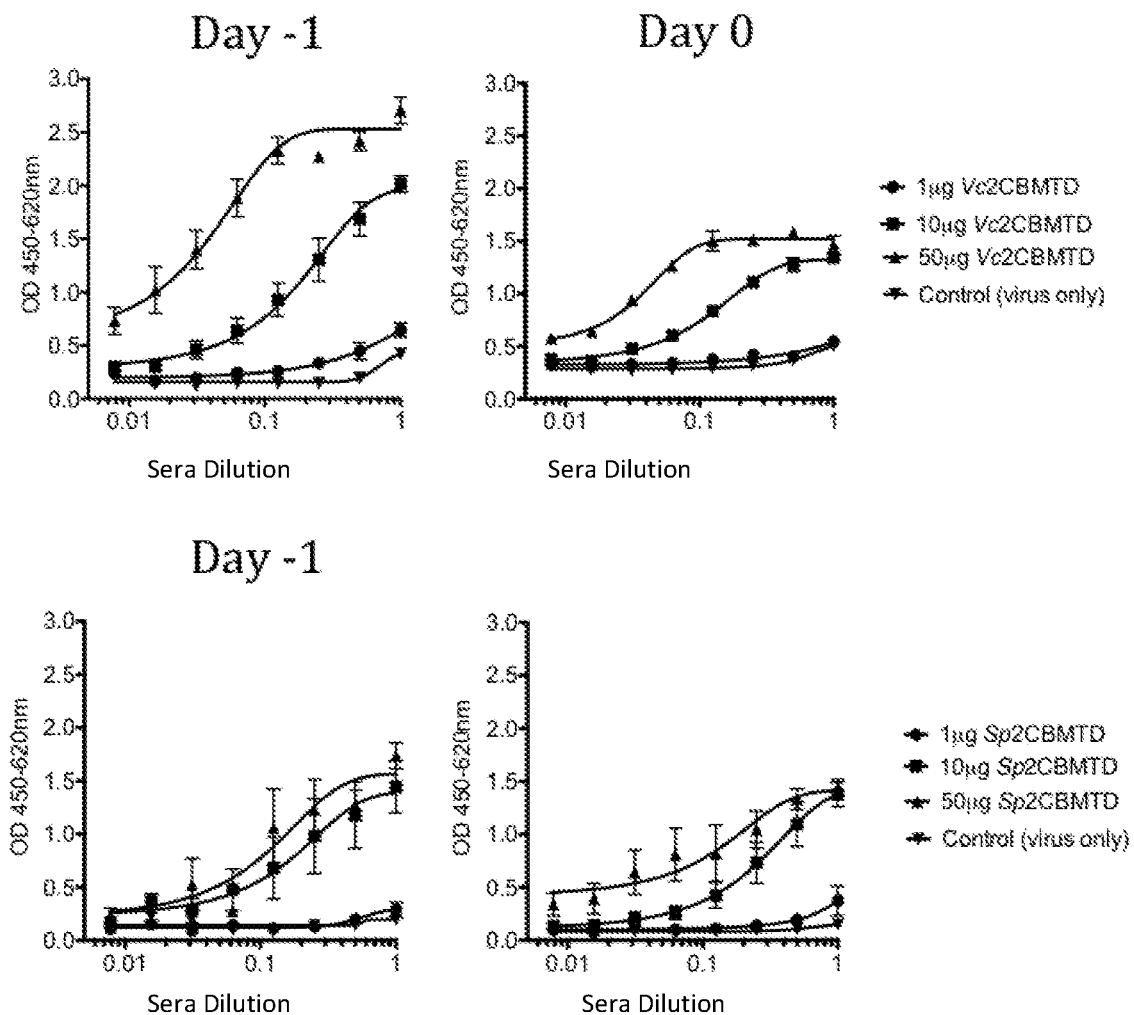

FIG. 2: Titration curves of mucosal anti-mCBM40 IgA antibodies in BAL mouse samples. Mice (groups of 5) were administered either 1 µg, 10 µg, or 50 µg of mCBM40 intranasally before (Day-1) or on the day (Day 0) of an IFV-challenge. Mice were culled day 7 post infection, and BAL samples were taken and assayed for anti-mCBM40 antibodies by ELISA.

Figure 3A:
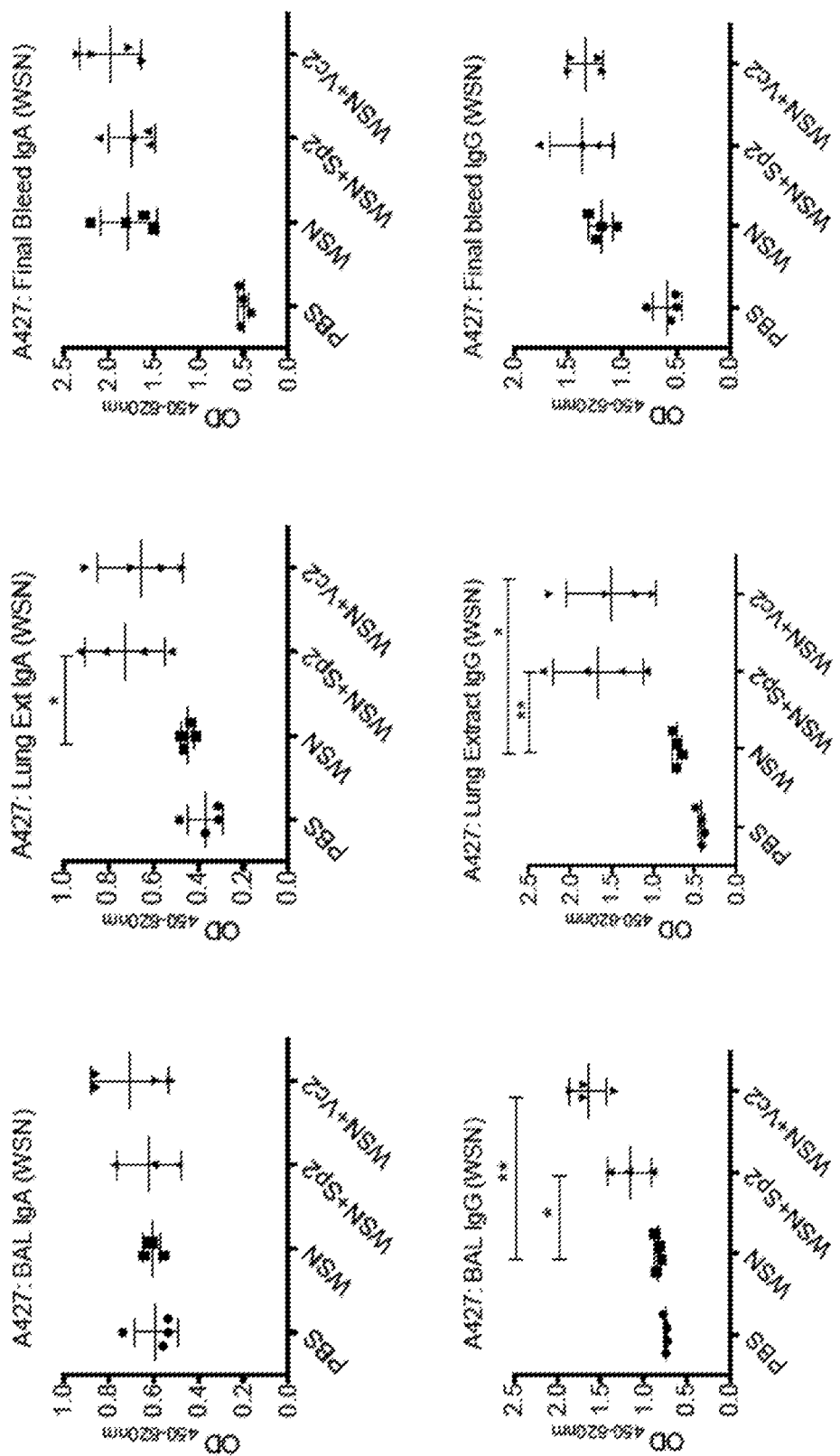
Figure 3B:
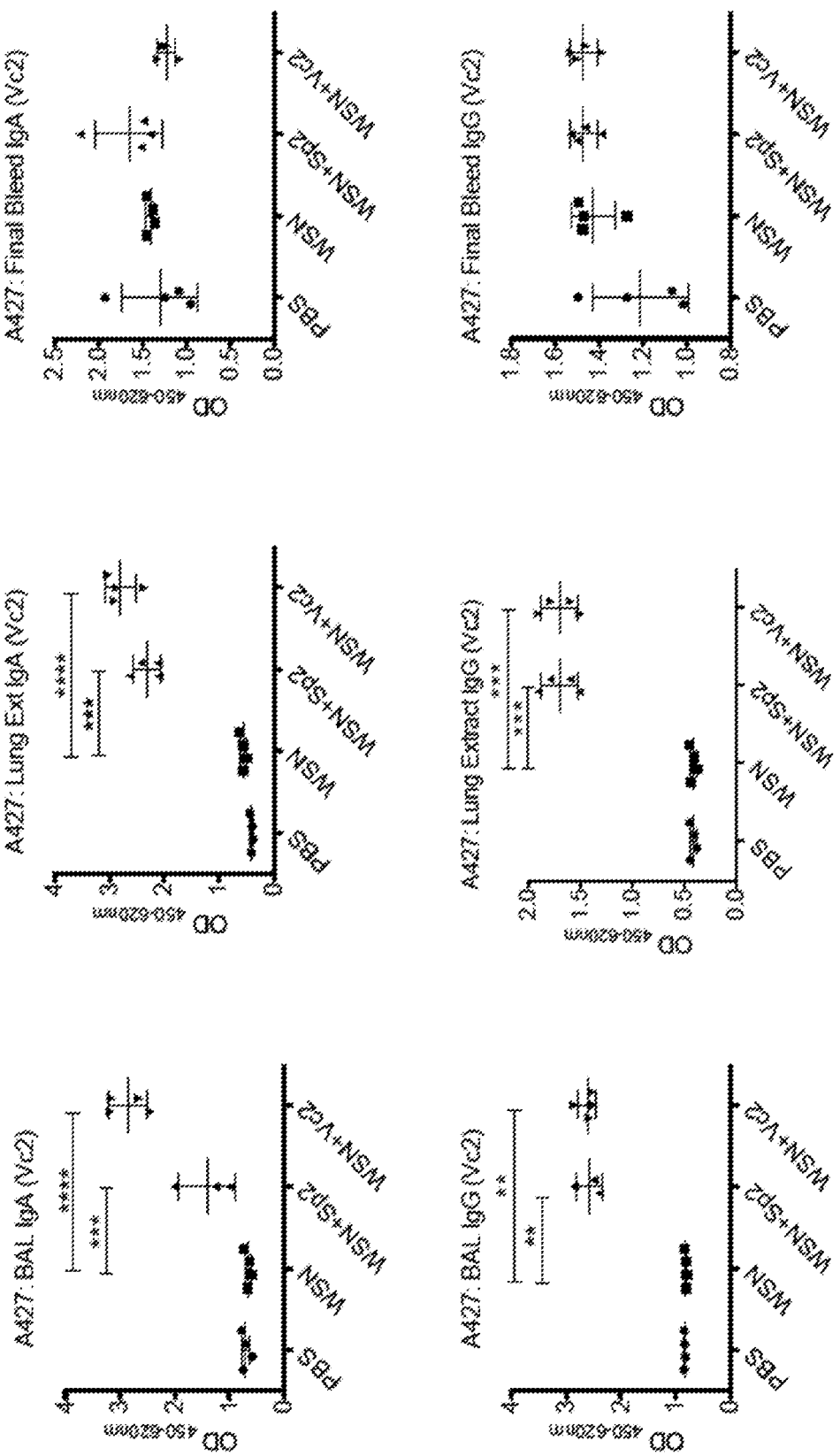
Figure 3C:
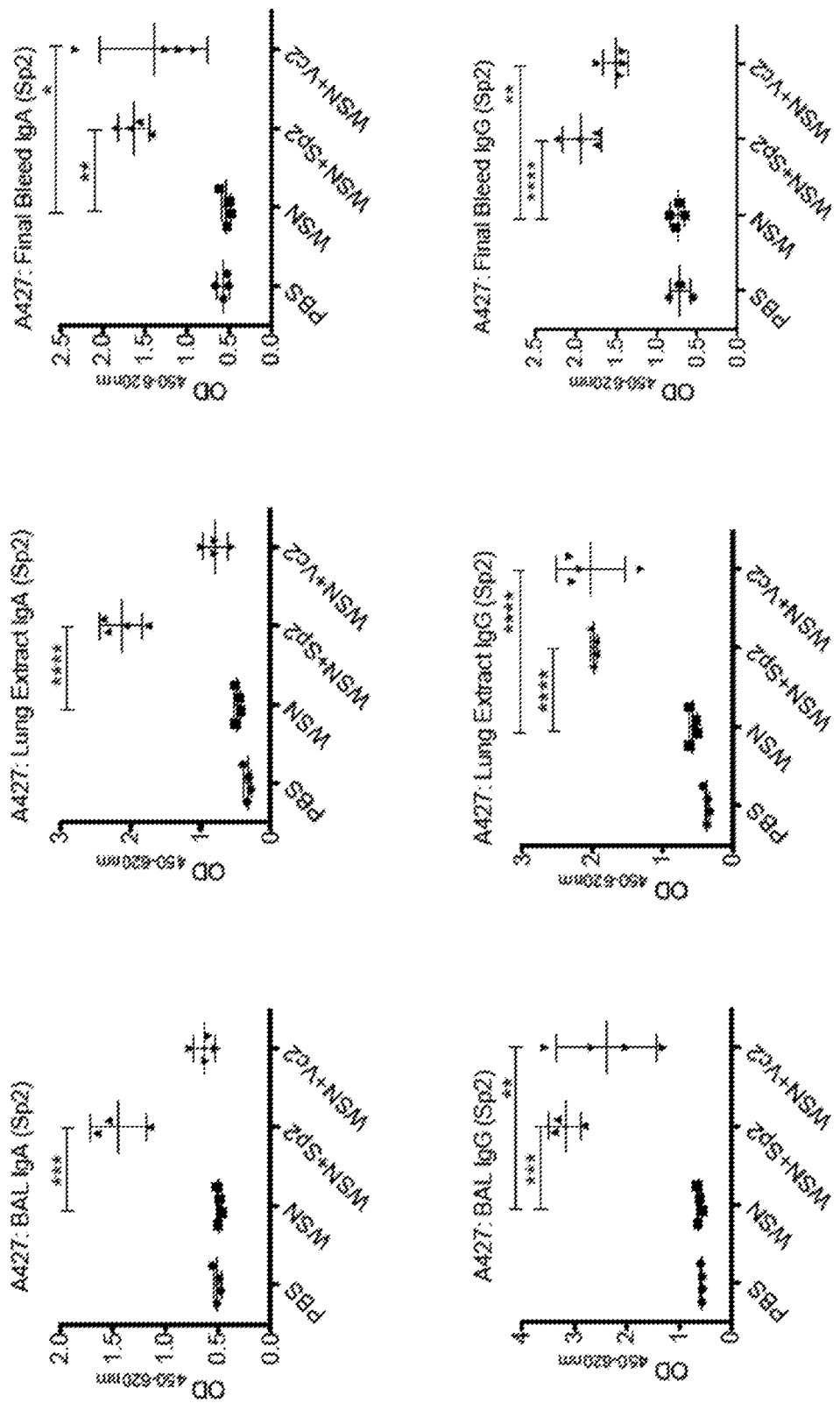

FIG. 3: Detection of IgA and IgG antibodies to IFV A/WSN/33 HA (a), Vc2CBMTD (b), and Sp2CBMTD (c), in mouse tissue. Tissue sample were obtained from a mouse study where mice were administered 1 µg of mCBM40 intranasally on Day 0, 14 and 27 before a viral challenge with 5000 PFU of IFV A/WSN/33 (H1N1) on Day 28. Mice were culled on Day 35 (i.e. day 7 post infection). BAL (1:10 diluted), lung extract (1:4) and sera (1:30) samples were assayed for the presence of both anti-mCBM40, and anti-viral HA antibodies by ELISA. Brackets indicate ELISA coat antigen. Data represent the mean±SD. Asterisks indicate P values of *<0.05, 0.01, *<0.001, ****<0.0001 of infected mice compared to treated, infected groups, using Bonferroni's t-test.

Figure 4A:
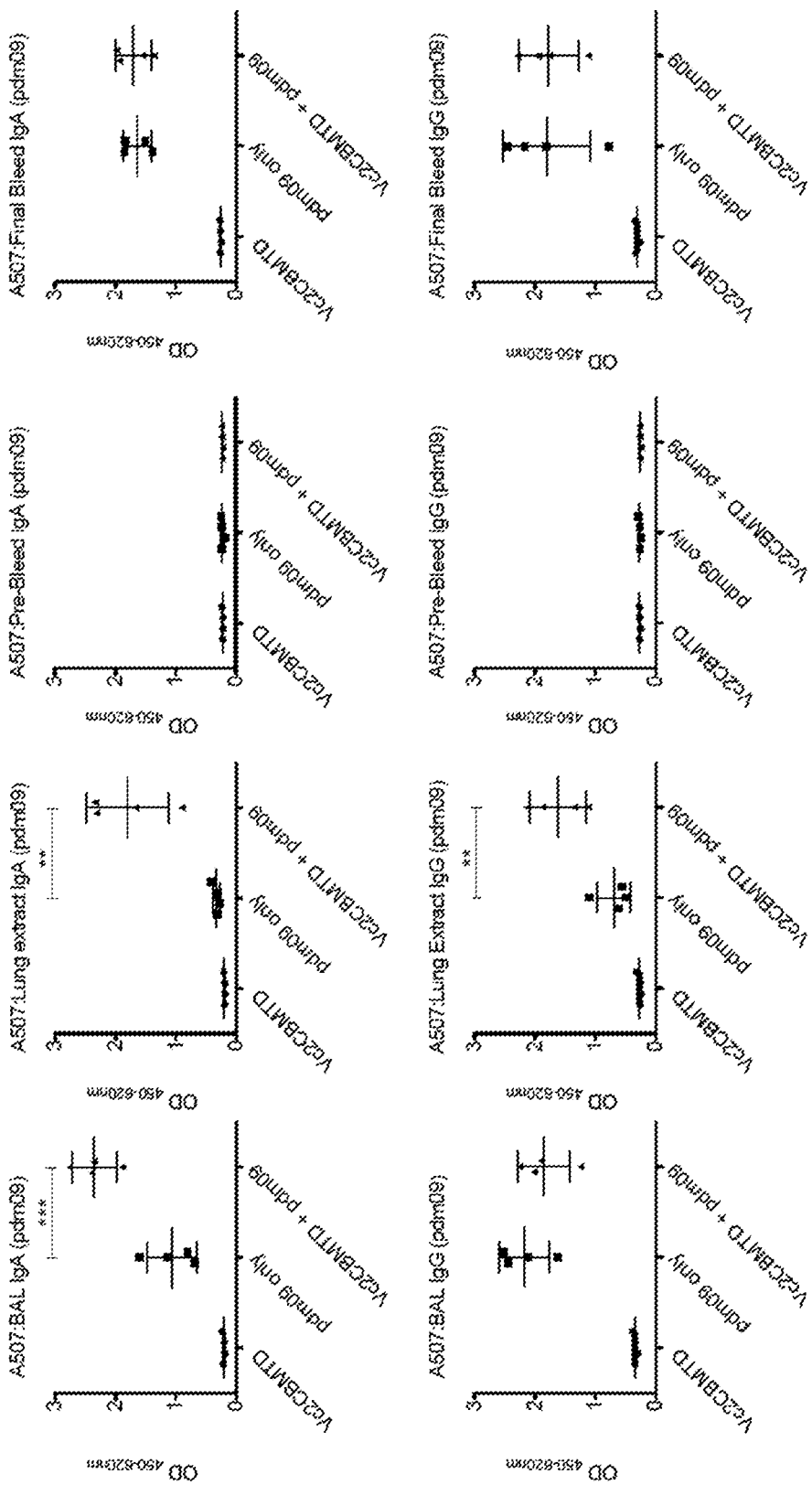
Figure 4B:
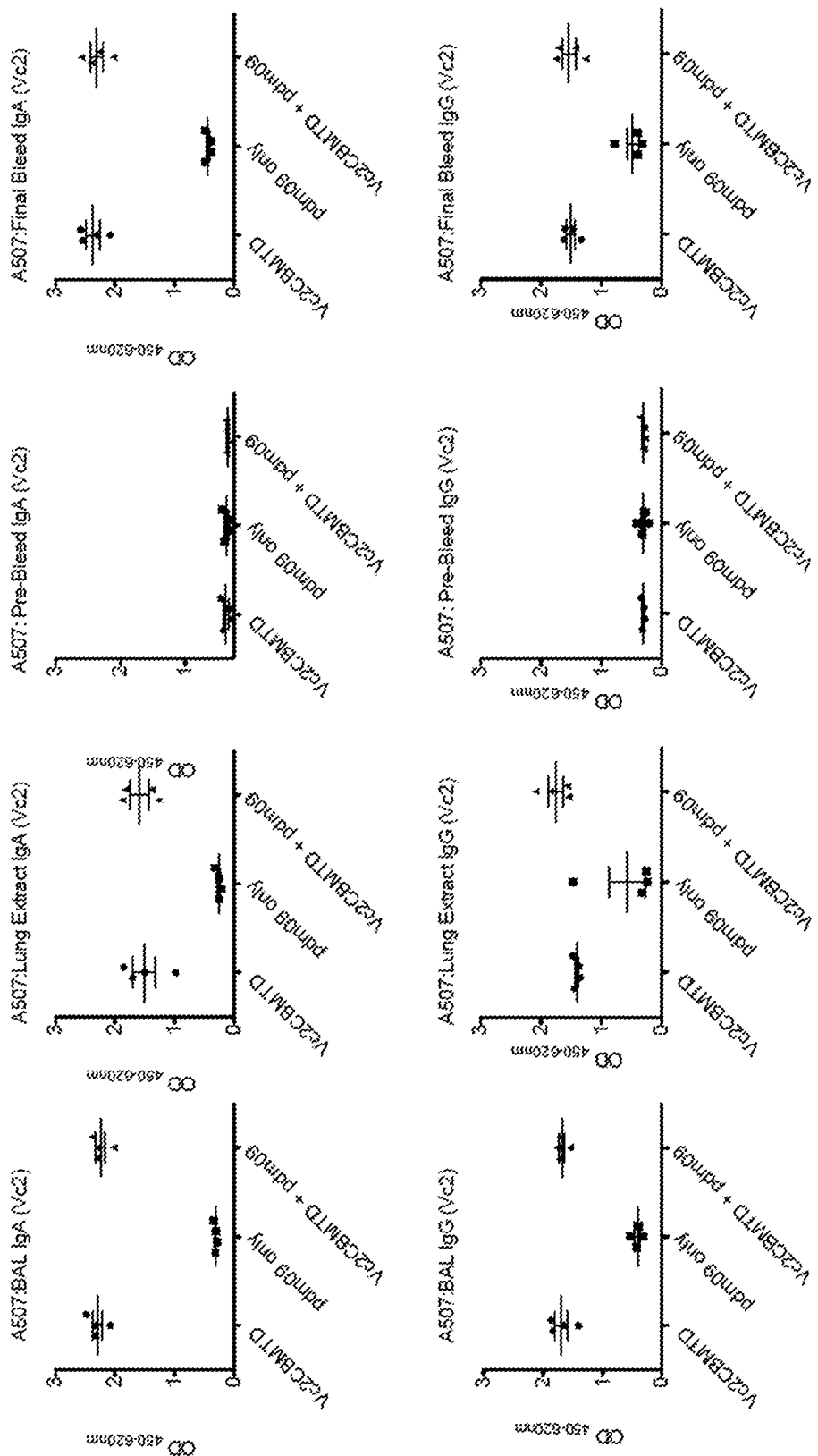

FIG. 4: Detection of IgA and IgG antibodies to IFV A/California/pdm09 HA (a), and Vc2CBMTD (b) in mouse tissue. Tissue sample were obtained from a mouse study where mice were administered 10 µg of mCBM40 intranasally on Day 0, 4 and 6 before a viral challenge with 150 PFU of IFV A/California/pdm09 (H1N1) on Day 7. Mice were culled around Day 21 (i.e. ~day 15 post infection), unless otherwise stated (see text). BAL (1:1 diluted), lung extract (1:5) and sera (1:30) samples were assayed for the presence of both antiviral HA antibodies and anti-mCBM40 by ELISA. Brackets indicate ELISA coat antigen. Data represent the mean±SD. Asterisks indicate P values of *<0.05, 0.01, *<0.001, ****<0.0001 of infected mice compared to treated, infected groups, using Bonferroni's t-test.

FIG. 5: Intranasal administration protocol. (A) Timeline of prime and boost intranasal inoculations of antigens in mice including sera sampling. (B) Table of dosing amounts of antigens. All mouse groups, with the exception of Group 1 (control), were treated with molar equivalent amounts of protein as represented by different amounts of protein given in 40 µL endotoxin-free PBS.

Figure 6A:
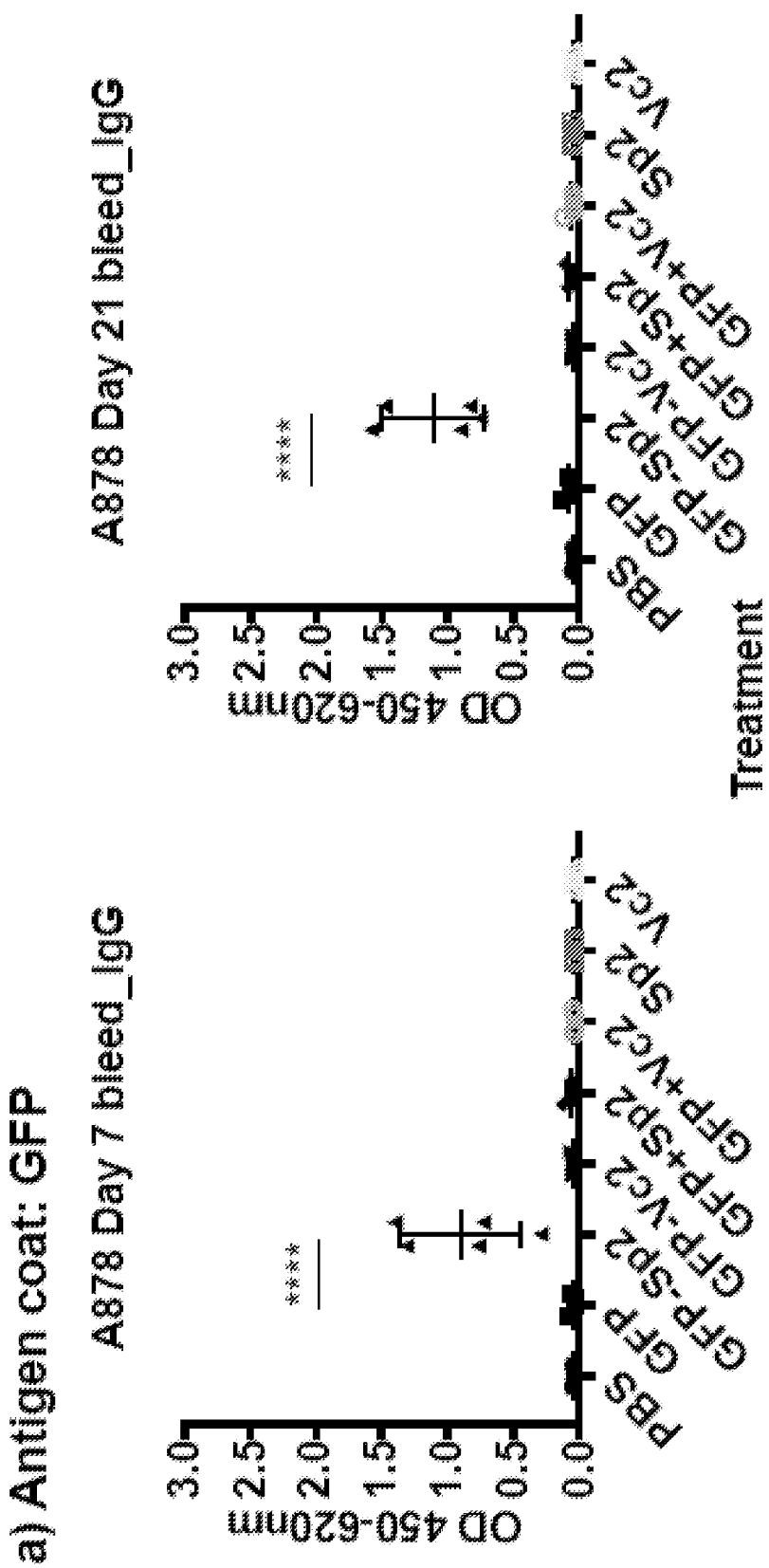
Figure 6B:
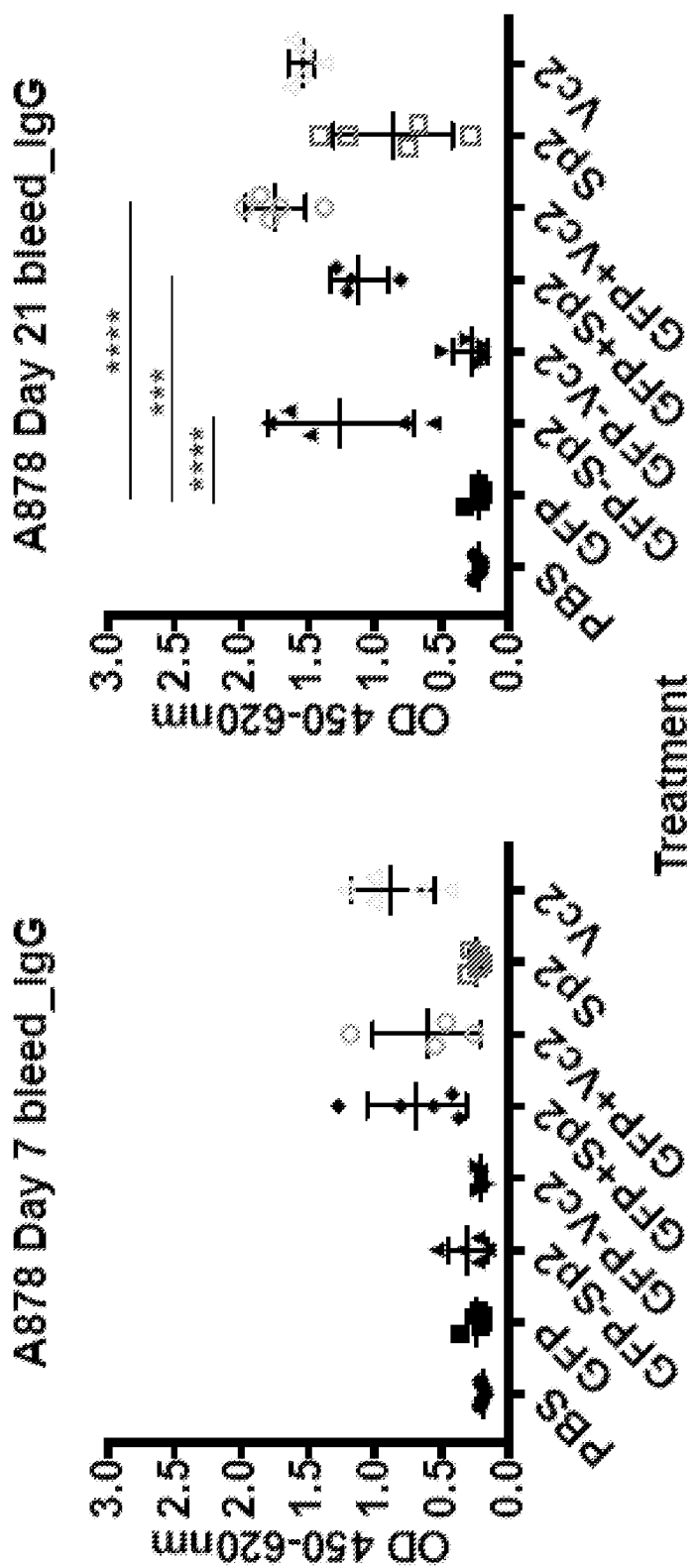
Figure 6C:
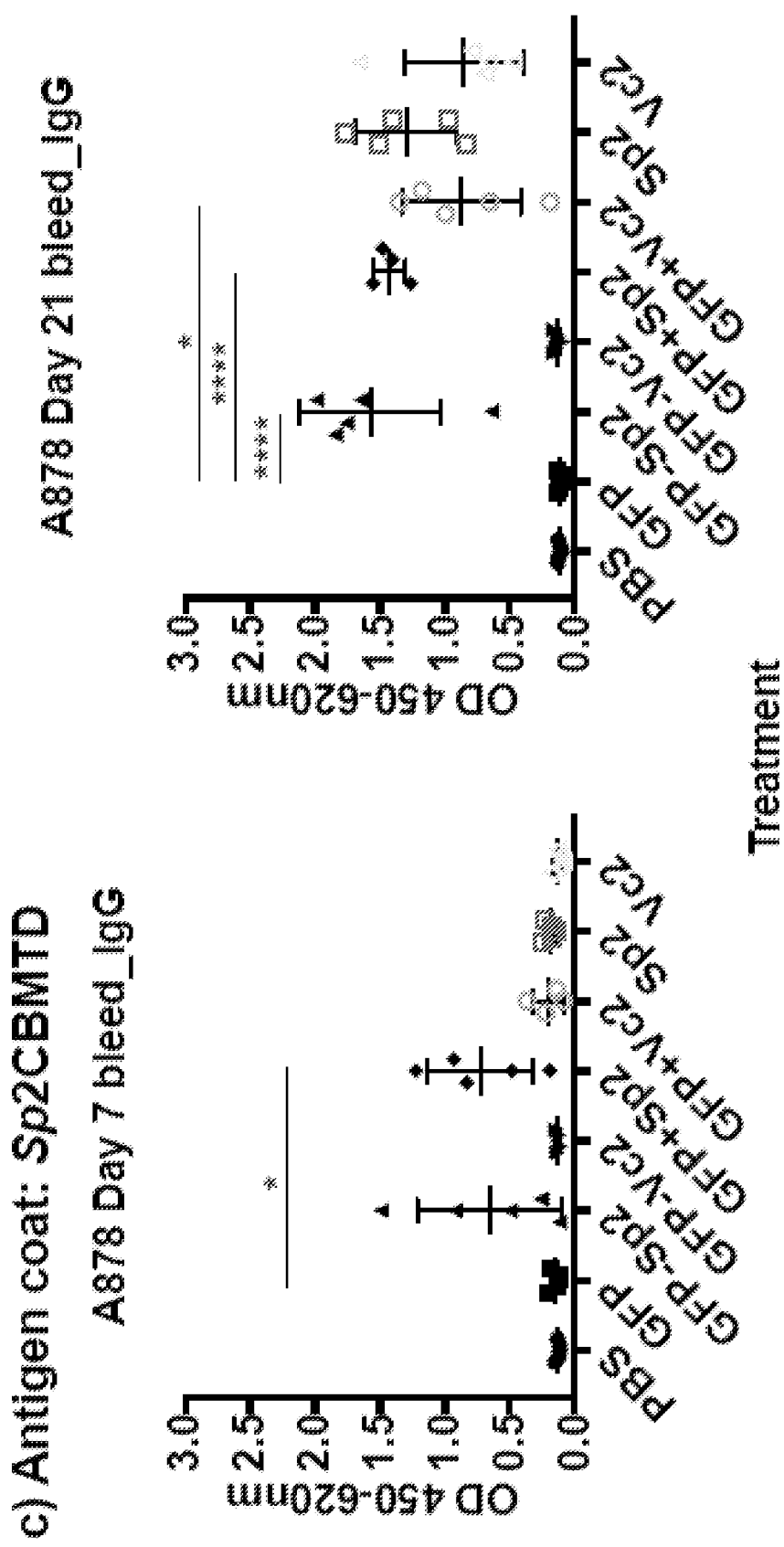

FIG. 6: Detection of sera IgG to GFP, Vc2CBMTD and Sp2CBMTD following intranasal administration in mice. Mice were intranasally administered up to 2 µg (40 µL) of antigen on day 0 and day 14. Sera were taken on days 7 and 21 to assess anti-GFP (A), anti-Vc2CBMTD (B) and anti-Sp2CBMTD (C) IgG antibodies by ELISA, as described in Methods. Bars indicate the mean absorbance change ±SD for IgG from five mice per group. All values are presented as mean±SD, with statistical results presented as: *p<0.05, p<0.01, *p<0.001, and ****p<0.0001.

FIG. 7. Detection of IgA and IgG to GFP, Vc2CBMTD and Sp2CBMTD from various tissues after intranasal treatment in mice. Mice were intranasally administered up to 2 µg (40 µL) of antigen on day 0, and day 14. Tissue samples (BAL, lung and sera) were taken on day 35 to assess anti-GFP (A), anti-Vc2CBMTD (B) and anti-Sp2CBMTD (C) IgG and IgA antibodies by ELISA, as described in Methods. Bars indicate the mean absorbance change ±SD for IgG or IgA from five mice per group. All values are presented as mean±SD, with statistical results presented as: *p<0.05, p<0.01, *p<0.001, and ****p<0.0001.

EXAMPLE 1

Materials and Methods

Standard ELISAs using immobilised biologics were used to analyse bronchiolar alveolar lavage (BAL) samples collected from a murine study where mCBM40s were given intranasally prior to a lethal influenza challenge. The mice were culled 7 days later.

In one study, mCBM40s were shown to elicit a strong mucosal IgA response in a dose-dependent manner (see FIG. 2). This suggests that mCBM40 are potent mucosal immunogens, similar to other bacterially-derived immunogens such as cholera toxin and LTB.

In another mouse study a low (1 µg) repeated dose of mCBM40 was administered up to a month before a IFV-challenge, with mice being culled 7 days later. Mouse tissues were analysed for evidence of IFV HA-specific, and mCBM40-specific antibodies from BAL, lung extracts and sera. We observed both anti-IFV HA IgA and IgG antibodies in BAL and lung extracts from mice that were treated with mCBM40s and that the levels of antibodies were increased in some of these mice compared to mice that were given virus only (see FIG. 3).

Despite mice being exposed to virus for only a week before culling, the data suggests that the mCBM40s, even at low doses, appear to enhance the level of antiviral antibodies in lung extracts. A similar murine study where mCBM40, Vc2CBMTD, was given to mice up to 1 week before a lethal IFV A/California/pdm09 challenge, and with mice culled approximately 2 weeks later, also showed the presence of both mCBM40 and antiviral IgA and IgG antibodies in BAL and lung homogenates (see FIG. 4).

The difference in antiviral HA antibodies between treated and untreated infected mice were statistically significant; however, some mice from the untreated, infected group were culled just before the designated cull date due to greater than 25% weight loss (around Days 9-11 post infection). Despite this, mCBM40s have the potential to be potent non-toxic, mucosal adjuvants for antigens or vaccines of interest, particularly for respiratory pathogens.

EXAMPLE 2

Introduction

When mCBM40s are administered in mice, they have been shown to be non-toxic, and capable of generating protective immune responses against respiratory pathogens, such as an influenza virus (IFV), that target cell surface sialic acid-receptors during infection (PNAS (2014) 111, 6401; AAC (2015) 59, 1495). Analyses of mucosal tissue from mice infected with IFV indicate that mCBM40s are also potent immunogens and appear to enhance an IFV antigen-specific antibody response when mCBM40s are directed to the same tissue. Based on these findings, we investigated whether the immune response of a test antigen is enhanced through the use of a CBM-based adjuvant.

Methods

Intranasal immunization of mice. All CBM40 proteins were prepared as described in PNAS (2014) 111, 6401. Female BALB/c mice (6-week old) were used for the study. All intranasal inoculations and mice bleeds were performed under isofluorane anaesthesia. The immunization schedule and bleeds were performed as outlined in FIG. 5. Eight groups of mice (n=5) were pre-bled (via tail) one week before an initial dose of purified recombinant protein (up to 2 µg purified proteins in 40 µl sterile endotoxin free PBS), was given intranasally. At day 14, mice were given a further intranasal dose of antigens. Mice were weighed on day 0 and day 14 and on days 1 & 2 after dosing to monitor any effects of dosing. Mice were also monitored throughout for clinical signs. On day 35, mice were culled by rising $CO_2$, and BAL fluid, lungs and serum, harvested for analysis.

Antibody Analysis.

Immune samples (BAL, lungs and sera) were analysed for the presence of anti-GFP antibodies and anti-mCBM40 antibodies using the ELISA technique as described in PNAS (2014) 111, 6401. For this, antigens (1 µg per well) were immobilized on 96-well plates (Corning). Tissue samples were diluted in blocking buffer as followed: BAL (1:4), homogenized lung tissue (1:4) and sera (1:50). Samples were added to wells followed by goat anti-mouse IgG, IgA, or IgM HRP-conjugate antibodies (Santa Cruz, 1:5000 dilution), and the presence of antibodies was detected using TMB (Sigma). Absorbance was measured at the 450-nm wavelength (620-nm wavelength used as reference).

Statistical Analysis.

Pairwise comparisons were made using one-way ANOVA and Tukey's multiple comparisons test. GraphPad Prism 7 (GraphPad Software) was used for all analysis. Tests with $p<0.05$ were deemed statistically significant. Unless otherwise stated, all values are presented as mean±SD, with statistical results presented as: $*p<0.05$, $p<0.01$, $*p<0.001$, and $****p<0.0001$.

SUMMARY

1. Conjugation of the test antigen (GFP) to Sp2CBMTD, generated both local and systemic anti-GFP antibodies from 7 days post intranasal administration.

2. The conjugation method using Sp2CBMTD was more efficient in generating anti-GFP antibodies compared to either GFP alone or co-administration with Sp2CBMTD or Vc2CBMTD (FIGS. 6 and 7).

3. Mucosal IgA and IgG responses of both GFP and mCBM40 (Sp2CBMTD, Vc2CBMTD) in lung tissue and BAL were also observed after 35 days.

---

The invention claimed is:

1. A method of improving an immune response to an antigen in a human or animal subject, said method comprising administering a composition comprising the antigen and a molecule capable of binding sialic acid to said human or animal subject, wherein the molecule capable of binding sialic acid, is an adjuvant which improves the immune response to the antigen,
wherein the molecule capable of binding sialic acid comprises two or more family 40 carbohydrate binding modules.

2. The method of claim 1, wherein the immune response is a mucosal immune response.

3. The method of claim 1, wherein the composition is a vaccine.

4. The method of claim 1, wherein the composition is a mucosal vaccine.

5. The method of claim 1, wherein the molecule capable of binding sialic acid is fused, linked or conjugated to the antigen.

6. The method of claim 1, wherein the molecule capable of binding sialic acid is fused to an internal region of the antigen and/or to the N- and/or C-terminal region of the antigen.

7. The method of claim 1, wherein the antigen is one or more selected from the group consisting of:
(i) (a) bacterial antigen(s);
(ii) (a) viral antigen(s);
(iii) (a) vaccine antigen(s); and
(iv) (a) cancer/tumour antigen(s).

8. The method of claim 1, wherein the adjuvant comprises the sialic acid binding domain of *Vibrio cholerae* NanH sialidase and/or the sialic acid binding domain of *Streptococcus pneumoniae* NanA sialidase.

9. The method of claim 1, wherein the adjuvant comprises the *Vibrio cholerae* NanH sialidase amino acid sequence of SEQ ID NO: 1 or 2.

10. The method of claim 1, wherein the adjuvant comprises the *Streptococcus pneumoniae* NanA sialidase amino acid sequence of SEQ ID NO: 3 or 4.

11. The method of claim 1, wherein the adjuvant is Vc2CBMTD, wherein Vc2CBMTD is two sialic acid binding domains from *Vibrio cholerae* NanH sialidase (Vc2CBM) fused, bound or conjugated to *Pseudomonas aeruginosa* pseudaminidase trimerisation domain (TD), wherein the sequence of each sialic acid binding domain from *Vibrio cholerae* NanH sialidase is SEQ ID NO: 2 and the sequence of the trimerisation domain is SEQ ID NO: 6.

12. The method of claim 1, wherein the adjuvant is Sp2CBMTD, wherein Sp2CBMTD is two sialic acid binding domains from *Streptococcus pneumoniae* NanA sialidase (Sp2CBM) fused, bound or conjugated to *Pseudomonas aeruginosa* pseudaminidase trimerisation domain (TD) wherein the sequence of each sialic acid binding domain from *Streptococcus pneumoniae* NanA sialidase is SEQ ID NO: 4 and the sequence of the trimerisation domain is SEQ ID NO: 6.

* * * * *

UNITED STATES PATENT AND TRADEMARK OFFICE
CERTIFICATE OF CORRECTION

PATENT NO. : 11,406,704 B2
APPLICATION NO. : 16/332917
DATED : August 9, 2022
INVENTOR(S) : Connaris et al.

It is certified that error appears in the above-identified patent and that said Letters Patent is hereby corrected as shown below:

On the Title Page

(30) Foreign Application Priority Data: Please correct "1616007" to read --1616007.9--

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 11

<210> SEQ ID NO 1
<211> LENGTH: 781
<212> TYPE: PRT
<213> ORGANISM: Vibrio cholerae

<400> SEQUENCE: 1

```
Met Arg Phe Lys Asn Val Lys Lys Thr Ala Leu Met Leu Ala Met Phe
1               5                   10                  15

Gly Met Ala Thr Ser Ser Asn Ala Ala Leu Phe Asp Tyr Asn Ala Thr
            20                  25                  30

Gly Asp Thr Glu Phe Asp Ser Pro Ala Lys Gln Gly Trp Met Gln Asp
        35                  40                  45

Asn Thr Asn Asn Gly Ser Gly Val Leu Thr Asn Ala Asp Gly Met Pro
    50                  55                  60

Ala Trp Leu Val Gln Gly Ile Gly Gly Arg Ala Gln Trp Thr Tyr Ser
65                  70                  75                  80

Leu Ser Thr Asn Gln His Ala Gln Ala Ser Ser Phe Gly Trp Arg Met
                85                  90                  95

Thr Thr Glu Met Lys Val Leu Ser Gly Gly Met Ile Thr Asn Tyr Tyr
            100                 105                 110

Ala Asn Gly Thr Gln Arg Val Leu Pro Ile Ile Ser Leu Asp Ser Ser
        115                 120                 125

Gly Asn Leu Val Val Glu Phe Glu Gly Gln Thr Gly Arg Thr Val Leu
    130                 135                 140

Ala Thr Gly Thr Ala Ala Thr Glu Tyr His Lys Phe Glu Leu Val Phe
145                 150                 155                 160

Leu Pro Gly Ser Asn Pro Ser Ala Ser Phe Tyr Phe Asp Gly Lys Leu
                165                 170                 175

Ile Arg Asp Asn Ile Gln Pro Thr Ala Ser Lys Gln Asn Met Ile Val
            180                 185                 190

Trp Gly Asn Gly Ser Ser Asn Thr Asp Gly Val Ala Ala Tyr Arg Asp
        195                 200                 205

Ile Lys Phe Glu Ile Gln Gly Asp Val Ile Phe Arg Gly Pro Asp Arg
    210                 215                 220
```

```
Ile Pro Ser Ile Val Ala Ser Val Thr Pro Val Val Thr Ala
225                 230                 235                 240

Phe Ala Glu Lys Arg Val Gly Gly Asp Pro Gly Ala Leu Ser Asn
                245                 250                 255

Thr Asn Asp Ile Ile Thr Arg Thr Ser Arg Asp Gly Ile Thr Trp
            260                 265                 270

Asp Thr Glu Leu Asn Leu Thr Glu Gln Ile Asn Val Ser Asp Glu Phe
        275                 280                 285

Asp Phe Ser Asp Pro Arg Pro Ile Tyr Asp Pro Ser Ser Asn Thr Val
    290                 295                 300

Leu Val Ser Tyr Ala Arg Trp Pro Thr Asp Ala Ala Gln Asn Gly Asp
305                 310                 315                 320

Arg Ile Lys Pro Trp Met Pro Asn Gly Ile Phe Tyr Ser Val Tyr Asp
                325                 330                 335

Val Ala Ser Gly Asn Trp Gln Ala Pro Ile Asp Val Thr Asp Gln Val
            340                 345                 350

Lys Glu Arg Ser Phe Gln Ile Ala Gly Trp Gly Gly Ser Glu Leu Tyr
        355                 360                 365

Arg Arg Asn Thr Ser Leu Asn Ser Gln Gln Asp Trp Gln Ser Asn Ala
370                 375                 380

Lys Ile Arg Ile Val Asp Gly Ala Ala Asn Gln Ile Gln Val Ala Asp
385                 390                 395                 400

Gly Ser Arg Lys Tyr Val Val Thr Leu Ser Ile Asp Glu Ser Gly Gly
                405                 410                 415

Leu Val Ala Asn Leu Asn Gly Val Ser Ala Pro Ile Ile Leu Gln Ser
            420                 425                 430

Glu His Ala Lys Val His Ser Phe His Asp Tyr Glu Leu Gln Tyr Ser
        435                 440                 445

Ala Leu Asn His Thr Thr Thr Leu Phe Val Asp Gly Gln Gln Ile Thr
450                 455                 460

Thr Trp Ala Gly Glu Val Ser Gln Glu Asn Asn Ile Gln Phe Gly Asn
465                 470                 475                 480

Ala Asp Ala Gln Ile Asp Gly Arg Leu His Val Gln Lys Ile Val Leu
                485                 490                 495

Thr Gln Gln Gly His Asn Leu Val Glu Phe Asp Ala Phe Tyr Leu Ala
            500                 505                 510

Gln Gln Thr Pro Glu Val Glu Lys Asp Leu Glu Lys Leu Gly Trp Thr
        515                 520                 525

Lys Ile Lys Thr Gly Asn Thr Met Ser Leu Tyr Gly Asn Ala Ser Val
530                 535                 540

Asn Pro Gly Pro Gly His Gly Ile Thr Leu Thr Arg Gln Gln Asn Ile
545                 550                 555                 560

Ser Gly Ser Gln Asn Gly Arg Leu Ile Tyr Pro Ala Ile Val Leu Asp
                565                 570                 575

Arg Phe Phe Leu Asn Val Met Ser Ile Tyr Ser Asp Asp Gly Gly Ser
            580                 585                 590

Asn Trp Gln Thr Gly Ser Thr Leu Pro Ile Pro Phe Arg Trp Lys Ser
        595                 600                 605

Ser Ser Ile Leu Glu Thr Leu Glu Pro Ser Glu Ala Asp Met Val Glu
610                 615                 620

Leu Gln Asn Gly Asp Leu Leu Leu Thr Ala Arg Leu Asp Phe Asn Gln
625                 630                 635                 640
```

```
Ile Val Asn Gly Val Asn Tyr Ser Pro Arg Gln Gln Phe Leu Ser Lys
                645                 650                 655

Asp Gly Gly Ile Thr Trp Ser Leu Leu Glu Ala Asn Asn Ala Asn Val
            660                 665                 670

Phe Ser Asn Ile Ser Thr Gly Thr Val Asp Ala Ser Ile Thr Arg Phe
        675                 680                 685

Glu Gln Ser Asp Gly Ser His Phe Leu Leu Phe Thr Asn Pro Gln Gly
    690                 695                 700

Asn Pro Ala Gly Thr Asn Gly Arg Gln Asn Leu Gly Leu Trp Phe Ser
705                 710                 715                 720

Phe Asp Glu Gly Val Thr Trp Lys Gly Pro Ile Gln Leu Val Asn Gly
                725                 730                 735

Ala Ser Ala Tyr Ser Asp Ile Tyr Gln Leu Asp Ser Glu Asn Ala Ile
            740                 745                 750

Val Ile Val Glu Thr Asp Asn Ser Asn Met Arg Ile Leu Arg Met Pro
        755                 760                 765

Ile Thr Leu Leu Lys Gln Lys Leu Thr Leu Ser Gln Asn
    770                 775                 780

<210> SEQ ID NO 2
<211> LENGTH: 192
<212> TYPE: PRT
<213> ORGANISM: Vibrio cholerae

<400> SEQUENCE: 2

Ala Leu Phe Asp Tyr Asn Ala Thr Gly Asp Thr Glu Phe Asp Ser Pro
1               5                  10                  15

Ala Lys Gln Gly Trp Met Gln Asp Thr Asn Asn Gly Ser Gly Val
                20                  25                  30

Leu Thr Asn Ala Asp Gly Met Pro Ala Trp Leu Val Gln Gly Ile Gly
            35                  40                  45

Gly Arg Ala Gln Trp Thr Tyr Ser Leu Ser Thr Asn Gln His Ala Gln
        50                  55                  60

Ala Ser Ser Phe Gly Trp Arg Met Thr Thr Glu Met Lys Val Leu Ser
65                  70                  75                  80

Gly Gly Met Ile Thr Asn Tyr Tyr Ala Asn Gly Thr Gln Arg Val Leu
                85                  90                  95

Pro Ile Ile Ser Leu Asp Ser Ser Gly Asn Leu Val Val Glu Phe Glu
            100                 105                 110

Gly Gln Thr Gly Arg Thr Val Leu Ala Thr Gly Thr Ala Ala Thr Glu
        115                 120                 125

Tyr His Lys Phe Glu Leu Val Phe Leu Pro Gly Ser Asn Pro Ser Ala
    130                 135                 140

Ser Phe Tyr Phe Asp Gly Lys Leu Ile Arg Asp Asn Ile Gln Pro Thr
145                 150                 155                 160

Ala Ser Lys Gln Asn Met Ile Val Trp Gly Asn Gly Ser Ser Asn Thr
                165                 170                 175

Asp Gly Val Ala Ala Tyr Arg Asp Ile Lys Phe Glu Ile Gln Gly Asp
            180                 185                 190

<210> SEQ ID NO 3
<211> LENGTH: 1035
<212> TYPE: PRT
<213> ORGANISM: Streptococcus pneumoniae
```

<400> SEQUENCE: 3

```
Met Ser Tyr Phe Arg Asn Arg Asp Ile Asp Ile Glu Arg Asn Ser Met
1               5                   10                  15

Asn Arg Ser Val Gln Glu Arg Lys Cys Arg Tyr Ser Ile Arg Lys Leu
            20                  25                  30

Ser Val Gly Ala Val Ser Met Ile Val Gly Ala Val Val Phe Gly Thr
        35                  40                  45

Ser Pro Val Leu Ala Gln Glu Gly Ala Ser Glu Gln Pro Leu Ala Asn
    50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Lys Ile Pro Arg Asp Tyr Tyr Ala
            100                 105                 110

Arg Asp Leu Glu Asn Val Glu Thr Val Ile Glu Lys Glu Asp Val Glu
            115                 120                 125

Thr Asn Ala Ser Asn Gly Gln Arg Val Asp Leu Ser Ser Glu Leu Asp
130                 135                 140

Lys Leu Lys Lys Leu Glu Asn Ala Thr Val His Met Glu Phe Lys Pro
145                 150                 155                 160

Asp Ala Lys Ala Pro Ala Phe Tyr Asn Leu Phe Ser Val Ser Ser Ala
                165                 170                 175

Thr Lys Lys Asp Glu Tyr Phe Thr Met Ala Val Tyr Asn Asn Thr Ala
            180                 185                 190

Thr Leu Glu Gly Arg Gly Ser Asp Gly Lys Gln Phe Tyr Asn Asn Tyr
            195                 200                 205

Asn Asp Ala Pro Leu Lys Val Lys Pro Gly Gln Trp Asn Ser Val Thr
210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
                245                 250                 255

Phe Ile Lys Asp Met Pro Asp Val Thr His Val Gln Ile Gly Ala Thr
            260                 265                 270

Lys Arg Ala Asn Asn Thr Val Trp Gly Ser Asn Leu Gln Ile Arg Asn
            275                 280                 285

Leu Thr Val Tyr Asn Arg Ala Leu Thr Pro Glu Glu Val Gln Lys Arg
290                 295                 300

Ser Gln Leu Phe Lys Arg Ser Asp Leu Glu Lys Leu Pro Glu Gly
305                 310                 315                 320

Ala Ala Leu Thr Glu Lys Thr Asp Ile Phe Glu Ser Gly Arg Asn Gly
                325                 330                 335

Lys Pro Asn Lys Asp Gly Ile Lys Ser Tyr Arg Ile Pro Ala Leu Leu
            340                 345                 350

Lys Thr Asp Lys Gly Thr Leu Ile Ala Gly Ala Asp Glu Arg Arg Leu
            355                 360                 365

His Ser Ser Asp Trp Gly Asp Ile Gly Met Val Ile Arg Arg Ser Glu
370                 375                 380

Asp Asn Gly Lys Thr Trp Gly Asp Arg Val Thr Ile Thr Asn Leu Arg
385                 390                 395                 400
```

```
Asp Asn Pro Lys Ala Ser Asp Pro Ser Ile Gly Ser Pro Val Asn Ile
                405                 410                 415

Asp Met Val Leu Val Gln Asp Pro Glu Thr Lys Arg Ile Phe Ser Ile
            420                 425                 430

Tyr Asp Met Phe Pro Glu Gly Lys Gly Ile Phe Gly Met Ser Ser Gln
        435                 440                 445

Lys Glu Glu Ala Tyr Lys Lys Ile Asp Gly Lys Thr Tyr Gln Ile Leu
    450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Asp
                485                 490                 495

Pro Val Lys Pro Ala Tyr Ser Asp Lys Gly Asp Leu Tyr Lys Gly Asn
                500                 505                 510

Gln Leu Leu Gly Asn Ile Tyr Phe Thr Thr Asn Lys Thr Ser Pro Phe
            515                 520                 525

Arg Ile Ala Lys Asp Ser Tyr Leu Trp Met Ser Tyr Ser Asp Asp Asp
        530                 535                 540

Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
                565                 570                 575

Arg Asn Gly Pro His Lys Gly Arg Ile Leu Ile Pro Val Tyr Thr Thr
                580                 585                 590

Asn Asn Val Ser His Leu Asn Gly Ser Gln Ser Ser Arg Ile Ile Tyr
            595                 600                 605

Ser Asp Asp His Gly Lys Thr Trp His Ala Gly Glu Ala Val Asn Asp
610                 615                 620

Asn Arg Gln Val Asp Gly Gln Lys Ile His Ser Ser Thr Met Asn Asn
625                 630                 635                 640

Arg Arg Ala Gln Asn Thr Glu Ser Thr Val Val Gln Leu Asn Asn Gly
                645                 650                 655

Asp Val Lys Leu Phe Met Arg Gly Leu Thr Gly Asp Leu Gln Val Ala
                660                 665                 670

Thr Ser Lys Asp Gly Gly Val Thr Trp Glu Lys Asp Ile Lys Arg Tyr
        675                 680                 685

Pro Gln Val Lys Asp Val Tyr Val Gln Met Ser Ala Ile His Thr Met
    690                 695                 700

His Glu Gly Lys Glu Tyr Ile Ile Leu Ser Asn Ala Gly Gly Pro Lys
705                 710                 715                 720

Arg Glu Asn Gly Met Val His Leu Ala Arg Val Glu Glu Asn Gly Glu
                725                 730                 735

Leu Thr Trp Leu Lys His Asn Pro Ile Gln Lys Gly Glu Phe Ala Tyr
            740                 745                 750

Asn Ser Leu Gln Glu Leu Gly Asn Gly Glu Tyr Gly Ile Leu Tyr Glu
        755                 760                 765

His Thr Glu Lys Gly Gln Asn Ala Tyr Thr Leu Ser Phe Arg Lys Phe
    770                 775                 780

Asn Trp Asp Phe Leu Ser Lys Asp Leu Ile Ser Pro Thr Glu Ala Lys
785                 790                 795                 800

Val Lys Arg Thr Arg Glu Met Gly Lys Gly Val Ile Gly Leu Glu Phe
                805                 810                 815
```

```
Asp Ser Glu Val Leu Val Asn Lys Ala Pro Thr Leu Gln Leu Ala Asn
                820                 825                 830

Gly Lys Thr Ala Arg Phe Met Thr Gln Tyr Asp Thr Lys Thr Leu Leu
            835                 840                 845

Phe Thr Val Asp Ser Glu Asp Met Gly Gln Lys Val Thr Gly Leu Ala
        850                 855                 860

Glu Gly Ala Ile Glu Ser Met His Asn Leu Pro Val Ser Val Ala Gly
865                 870                 875                 880

Thr Lys Leu Ser Asn Gly Met Asn Gly Ser Glu Ala Ala Val His Glu
                885                 890                 895

Val Pro Glu Tyr Thr Gly Pro Leu Gly Thr Ser Gly Glu Glu Pro Ala
            900                 905                 910

Pro Thr Val Glu Lys Pro Glu Tyr Thr Gly Pro Leu Gly Thr Ser Gly
        915                 920                 925

Glu Glu Pro Ala Pro Thr Val Glu Lys Pro Glu Tyr Thr Gly Pro Leu
930                 935                 940

Gly Thr Ala Gly Glu Glu Ala Pro Thr Val Glu Lys Pro Glu Phe
945                 950                 955                 960

Thr Gly Gly Val Asn Gly Thr Glu Pro Ala Val His Glu Ile Ala Glu
                965                 970                 975

Tyr Lys Gly Ser Asp Ser Leu Val Thr Leu Thr Thr Lys Glu Asp Tyr
            980                 985                 990

Thr Tyr Lys Ala Pro Leu Ala Gln Gln Ala Leu Pro Glu Thr Gly Asn
        995                 1000                1005

Lys Glu Ser Asp Leu Leu Ala Ser Leu Gly Leu Thr Ala Phe Phe
    1010                1015                1020

Leu Gly Leu Phe Thr Leu Gly Lys Lys Arg Glu Gln
    1025                1030                1035

<210> SEQ ID NO 4
<211> LENGTH: 185
<212> TYPE: PRT
<213> ORGANISM: Streptococcus pneumoniae

<400> SEQUENCE: 4

Val Ile Glu Lys Glu Asp Val Glu Thr Asn Ala Ser Asn Gly Gln Arg
1               5                   10                  15

Val Asp Leu Ser Ser Glu Leu Asp Lys Leu Lys Lys Leu Glu Asn Ala
            20                  25                  30

Thr Val His Met Glu Phe Lys Pro Asp Ala Lys Ala Pro Ala Phe Tyr
        35                  40                  45

Asn Leu Phe Ser Val Ser Ser Ala Thr Lys Lys Asp Glu Tyr Phe Thr
    50                  55                  60

Met Ala Val Tyr Asn Asn Thr Ala Thr Leu Glu Gly Arg Gly Ser Asp
65                  70                  75                  80

Gly Lys Gln Phe Tyr Asn Asn Tyr Asn Asp Ala Pro Leu Lys Val Lys
                85                  90                  95

Pro Gly Gln Trp Asn Ser Val Thr Phe Thr Val Glu Lys Pro Thr Ala
            100                 105                 110

Glu Leu Pro Lys Gly Arg Val Arg Leu Tyr Val Asn Gly Val Leu Ser
        115                 120                 125

Arg Thr Ser Leu Arg Ser Gly Asn Phe Ile Lys Asp Met Pro Asp Val
    130                 135                 140

Thr His Val Gln Ile Gly Ala Thr Lys Arg Ala Asn Asn Thr Val Trp
145                 150                 155                 160
```

```
Gly Ser Asn Leu Gln Ile Arg Asn Leu Thr Val Tyr Asn Arg Ala Leu
            165                 170                 175

Thr Pro Glu Glu Val Gln Lys Arg Ser
            180                 185

<210> SEQ ID NO 5
<211> LENGTH: 5
<212> TYPE: PRT
<213> ORGANISM: Artificial Sequence
<220> FEATURE:
<223> OTHER INFORMATION: Linker

<400> SEQUENCE: 5

Ala Leu Asn Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Linker

<400> SEQUENCE: 6

Leu Gln Ala Leu Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Linker

<400> SEQUENCE: 7

Gly Gly Asn Ser Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Linker

<400> SEQUENCE: 8

Ala Leu Asn Gly Ser Gly Gly Ser Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Linker

<400> SEQUENCE: 9

Leu Gln Ala Leu Gly Gly Gly Gly Ser Leu
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Linker
```

<400> SEQUENCE: 10

Ala Leu Asn Gly Ser Gly Gly Ser Gly Gly Gly Ser Gly
1               5                   10                  15

<210> SEQ ID NO 11
<211> LENGTH: 438
<212> TYPE: PRT
<213> ORGANISM: Pseudomonas aeruginosa

<400> SEQUENCE: 11

Met Asn Thr Tyr Phe Asp Ile Pro His Arg Leu Val Gly Lys Ala Leu
1               5                   10                  15

Tyr Glu Ser Tyr Tyr Asp His Phe Gly Gln Met Asp Ile Leu Ser Asp
                20                  25                  30

Gly Ser Leu Tyr Leu Ile Tyr Arg Arg Ala Thr Glu His Val Gly Gly
            35                  40                  45

Ser Asp Gly Arg Val Val Phe Ser Lys Leu Glu Gly Gly Ile Trp Ser
        50                  55                  60

Ala Pro Thr Ile Val Ala Gln Ala Gly Gly Gln Asp Phe Arg Asp Val
65                  70                  75                  80

Ala Gly Gly Thr Met Pro Ser Gly Arg Ile Val Ala Ala Ser Thr Val
                85                  90                  95

Tyr Glu Thr Gly Glu Val Lys Val Tyr Val Ser Asp Asp Ser Gly Val
            100                 105                 110

Thr Trp Val His Lys Phe Thr Leu Ala Arg Gly Gly Ala Asp Tyr Asn
        115                 120                 125

Phe Ala His Gly Lys Ser Phe Gln Val Gly Ala Arg Tyr Val Ile Pro
    130                 135                 140

Leu Tyr Ala Ala Thr Gly Val Asn Tyr Glu Leu Lys Trp Leu Glu Ser
145                 150                 155                 160

Ser Asp Gly Gly Glu Thr Trp Gly Glu Gly Ser Thr Ile Tyr Ser Gly
                165                 170                 175

Asn Thr Pro Tyr Asn Glu Thr Ser Tyr Leu Pro Val Gly Asp Gly Val
            180                 185                 190

Ile Leu Ala Val Ala Arg Val Gly Ser Gly Ala Gly Gly Ala Leu Arg
        195                 200                 205

Gln Phe Ile Ser Leu Asp Asp Gly Gly Thr Trp Thr Asp Gln Gly Asn
    210                 215                 220

Val Thr Ala Gln Asn Gly Asp Ser Thr Asp Ile Leu Val Ala Pro Ser
225                 230                 235                 240

Leu Ser Tyr Ile Tyr Ser Glu Gly Gly Thr Pro His Val Val Leu Leu
                245                 250                 255

Tyr Thr Asn Arg Thr Thr His Phe Cys Tyr Tyr Arg Thr Ile Leu Leu
            260                 265                 270

Ala Lys Ala Val Ala Gly Ser Ser Gly Trp Thr Glu Arg Val Pro Val
        275                 280                 285

Tyr Ser Ala Pro Ala Ala Ser Gly Tyr Thr Ser Gln Val Val Leu Gly
    290                 295                 300

Gly Arg Arg Ile Leu Gly Asn Leu Phe Arg Glu Thr Ser Ser Thr Thr
305                 310                 315                 320

Ser Gly Ala Tyr Gln Phe Glu Val Tyr Leu Gly Gly Val Pro Asp Phe
                325                 330                 335

Glu Ser Asp Trp Phe Ser Val Ser Ser Asn Ser Leu Tyr Thr Leu Ser
            340                 345                 350

```
His Gly Leu Gln Arg Ser Pro Arg Arg Val Val Glu Phe Ala Arg
        355                 360                 365

Ser Ser Ser Pro Ser Thr Trp Asn Ile Val Met Pro Ser Tyr Phe Asn
    370                 375                 380

Asp Gly Gly His Lys Gly Ser Gly Ala Gln Val Glu Val Gly Ser Leu
385                 390                 395                 400

Asn Ile Arg Leu Gly Thr Gly Ala Ala Val Trp Gly Thr Gly Tyr Phe
                405                 410                 415

Gly Gly Ile Asp Asn Ser Ala Thr Thr Arg Phe Ala Thr Gly Tyr Tyr
            420                 425                 430

Arg Val Arg Ala Trp Ile
            435
```